US006475644B1

(12) United States Patent
Hampikian et al.

(10) Patent No.: US 6,475,644 B1
(45) Date of Patent: Nov. 5, 2002

(54) RADIOACTIVE COATING SOLUTIONS METHODS, AND SUBSTRATES

(75) Inventors: Janet M. Hampikian, Decatur; Neal A. Scott, Stone Mountain, both of GA (US)

(73) Assignee: Radiovascular Systems, L.L.C., Atlanta, GA (US)

( * ) Notice: Subject to any disclaimer, the term of this patent is extended or adjusted under 35 U.S.C. 154(b) by 0 days.

(21) Appl. No.: 09/386,779

(22) Filed: Aug. 31, 1999

Related U.S. Application Data
(60) Provisional application No. 60/141,766, filed on Jun. 30, 1999, and provisional application No. 60/108,963, filed on Nov. 18, 1998.

(51) Int. Cl.[7] .................. B23B 15/00; C23C 18/54; C25D 5/00; B05D 1/18; A61M 25/00
(52) U.S. Cl. ............... 428/655; 106/1.12; 106/1.13; 106/1.15; 106/1.18; 106/1.21; 106/1.27; 205/80; 205/170; 205/181; 205/187; 205/188; 205/191; 205/197; 205/261; 427/5; 427/304; 427/305; 427/405; 427/437; 428/680; 428/686; 428/457; 428/926; 428/935; 428/936; 604/509; 606/7
(58) Field of Search ................... 428/680, 686, 428/655, 457, 926, 935, 936; 427/5, 304, 305, 405, 437; 205/80, 170, 181, 187, 188, 191, 197, 261; 600/1, 3; 604/509; 606/7; 106/1.12, 1.13, 1.15, 1.18, 1.21, 1.27

(56) References Cited

U.S. PATENT DOCUMENTS

| 2,976,181 A | 3/1961 | Brookshire | 106/1.26 |
| 3,567,943 A | 3/1971 | Wallhausen et al. | 376/423 |

(List continued on next page.)

FOREIGN PATENT DOCUMENTS

| JP | 8-197316 | 8/1996 |
| JP | 10 039094 | 2/1998 |

(List continued on next page.)

OTHER PUBLICATIONS

Ali, Hassan O., et al., "A Review of Electroless Gold Deposition Processes", Gold Bull., 1984, 17, (4), pp. 118–127, no month.

Dini, J.W., "Developments and Trends in Electrodeposition", Sampe Quarterly, Apr. 1989, pp. 28–32.

(List continued on next page.)

Primary Examiner—Robert R. Koehler
(74) Attorney, Agent, or Firm—Finnegan, Henderson, Farabow, Garrett & Dunner, L.L.P.

(57) ABSTRACT

Radioactive coating solutions and sol-gels, and corresponding methods for making a substrate radioactive by the application of the radioactive coating solutions and sol-gels thereto. The radioactive coating solution comprises at least one carrier metal and a radioisotope, which may be soluble or insoluble, and may further comprise a reducing agent. The radioactive sol-gel comprises at least one metal alkoxide and a radioisotope, which may be soluble or insoluble. Methods of making a substrate radioactive by coating with radioactive coating solutions or sol-gels are also disclosed, including electrodeposition, electroless deposition, spin coating and dip coating. In a particular embodiment, the radioactive coating formed by the method is a composite coating. Radioactive substrates are also disclosed, comprising a substrate and one or more radioactive coatings, which coatings may be the same or different. Suitable substrates include medical devices, such as catheters, stents, brachytherapy devices and guidewires, or components thereof. Medical devices capable of generating asymmetric, or targeted, radiation fields are also disclosed.

208 Claims, 8 Drawing Sheets

U.S. PATENT DOCUMENTS

| | | | |
|---|---|---|---|
| 3,723,612 A | 3/1973 | Mikheev et al. | 252/634 |
| 3,767,434 A | 10/1973 | Thomas | 501/54 |
| 3,811,426 A | 5/1974 | Culver et al. | 250/493.1 |
| 3,844,833 A | 10/1974 | Drabkina et al. | 376/414 |
| 3,922,207 A | 11/1975 | Lowrey, Jr. et al. | 204/217 |
| 3,974,322 A | 8/1976 | Drabkina et al. | 250/493.1 |
| RE29,066 E | 12/1976 | Evans | 250/303 |
| 4,085,010 A | 4/1978 | Ishimori et al. | 204/237 |
| 4,173,981 A | 11/1979 | Mortensen | 604/8 |
| 4,229,300 A | 10/1980 | Benes et al. | 210/104 |
| 4,323,055 A | 4/1982 | Kubiatowicz | 376/169 |
| 4,331,551 A | 5/1982 | Berton et al. | 210/682 |
| 4,349,421 A | 9/1982 | Khattab | 205/926 |
| 4,440,801 A | 4/1984 | Aviram et al. | 427/306 |
| 4,441,965 A | 4/1984 | Matsumura et al. | 204/273 |
| 4,444,836 A | 4/1984 | Khattab | 427/305 |
| 4,481,081 A | 11/1984 | Doubt | 205/117 |
| 4,503,568 A | 3/1985 | Madras | 623/1.3 |
| 4,545,373 A | 10/1985 | Christoudias | 606/148 |
| 4,588,395 A | 5/1986 | Lemelson | 600/7 |
| 4,592,808 A | 6/1986 | Doubt | 205/117 |
| 4,643,891 A | 2/1987 | Panek | 252/645 |
| 4,670,306 A | 6/1987 | Salem | 427/304 |
| 4,752,415 A | 6/1988 | Iwaskow et al. | 252/502 |
| 4,781,198 A | 11/1988 | Kanabrocki | 600/562 |
| 4,819,618 A | 4/1989 | Liprie | 228/138 |
| 4,861,520 A | 8/1989 | van't Hooft et al. | 252/645 |
| 4,921,731 A | 5/1990 | Clark et al. | 427/318 |
| 4,940,609 A | 7/1990 | Tschang et al. | 427/305 |
| 5,019,075 A | 5/1991 | Spears et al. | 604/913 |
| 5,039,550 A | 8/1991 | Malghan et al. | 427/214 |
| 5,053,033 A | 10/1991 | Clarke | 606/15 |
| 5,059,166 A | 10/1991 | Fischell et al. | 424/1.11 |
| 5,061,245 A | 10/1991 | Waldvogel | 604/170.01 |
| 5,061,476 A | 10/1991 | Simon et al. | 252/635 |
| 5,084,299 A | 1/1992 | Hirsch et al. | 216/87 |
| 5,124,007 A | 6/1992 | Tsuchiya et al. | 205/259 |
| 5,137,709 A | 8/1992 | Simon et al. | 252/625 |
| 5,163,896 A | 11/1992 | Suthanthiran et al. | 600/8 |
| 5,175,027 A | 12/1992 | Holmes-Farley et al. | 427/388.4 |
| 5,176,617 A | 1/1993 | Fischell et al. | 600/3 |
| 5,182,143 A | 1/1993 | Holmes-Farley et al. | 427/410 |
| 5,199,939 A | 4/1993 | Dake et al. | 600/3 |
| 5,213,561 A | 5/1993 | Weinstein et al. | 600/3 |
| 5,230,927 A | 7/1993 | Nishizawa et al. | 427/305 |
| 5,232,744 A | 8/1993 | Nakamura et al. | 106/1.27 |
| 5,266,181 A | 11/1993 | Matsumura et al. | 427/437 |
| 5,267,960 A | 12/1993 | Hayman et al. | 600/3 |
| 5,269,838 A | 12/1993 | Inoue et al. | 106/1.27 |
| 5,271,955 A | 12/1993 | Maniar | 427/100 |
| 5,295,493 A | 3/1994 | Radisch, Jr. | 606/180 |
| 5,342,283 A | 8/1994 | Good | 376/158 |
| 5,364,459 A | 11/1994 | Senda et al. | 106/1.23 |
| 5,383,928 A | 1/1995 | Scott et al. | 606/194 |
| 5,385,760 A | 1/1995 | Schassberger et al. | 205/109 |
| 5,395,651 A | 3/1995 | Sodervall et al. | 427/305 |
| 5,396,141 A | 3/1995 | Jantz et al. | 136/253 |
| 5,401,369 A | 3/1995 | Gershin | 204/271 |
| 5,401,535 A | 3/1995 | Bishop | 427/229 |
| 5,405,309 A | 4/1995 | Carden, Jr. | 376/158 |
| 5,452,733 A | 9/1995 | Sterman et al. | 606/7 |
| 5,458,574 A | 10/1995 | Machold et al. | 604/509 |
| 5,484,384 A | 1/1996 | Fearnot | 600/3 |
| 5,503,613 A | 4/1996 | Weinberger | 600/436 |
| 5,516,388 A | 5/1996 | Moran et al. | 156/230 |
| 5,520,791 A | 5/1996 | Murase | 205/109 |
| 5,540,659 A | 7/1996 | Teirstein | 600/3 |
| 5,556,389 A | 9/1996 | Liprie | 600/434 |
| 5,558,701 A | 9/1996 | Patel | 106/35 |
| 5,584,803 A | 12/1996 | Stevens et al. | 604/101.01 |
| 5,616,114 A | 4/1997 | Thornton et al. | 600/3 |
| 5,618,266 A | 4/1997 | Liprie | 600/3 |
| 5,637,135 A | 6/1997 | Ottenstein et al. | 55/524 |
| 5,643,171 A | 7/1997 | Bradshaw et al. | 600/3 |
| 5,653,683 A | 8/1997 | D'Andrea | 600/2 |
| 5,658,282 A | 8/1997 | Daw et al. | 606/159 |
| 5,660,704 A | 8/1997 | Murase | 205/131 |
| 5,662,580 A | 9/1997 | Bradshaw et al. | 600/3 |
| 5,679,318 A | 10/1997 | Vanderheyden et al. | 424/1.45 |
| 5,683,345 A | 11/1997 | Waksman et al. | 600/3 |
| 5,695,469 A | 12/1997 | Segal | 604/509 |
| 5,702,368 A | 12/1997 | Stevens et al. | 604/170.03 |
| 5,702,584 A | 12/1997 | Goenka et al. | 205/164 |
| 5,707,332 A | 1/1998 | Weinberger | 600/3 |
| 5,713,828 A | 2/1998 | Coniglione | 600/7 |
| 5,722,984 A | 3/1998 | Fischell et al. | 600/3 |
| 5,735,290 A | 4/1998 | Sterman et al. | 604/500 |
| 5,750,203 A | 5/1998 | Chung | 427/387 |
| 5,755,708 A | 5/1998 | Segal | 604/104 |
| 5,766,151 A | 6/1998 | Valley et al. | 606/194 |
| 5,769,812 A | 6/1998 | Stevens et al. | 604/509 |
| 5,782,740 A | 7/1998 | Schneiderman | 604/524 |
| 5,782,742 A | 7/1998 | Crocker et al. | 600/3 |
| 5,824,622 A | 10/1998 | Harmer et al. | 502/158 |
| 5,840,615 A | 11/1998 | Aoki et al. | 427/419.5 |
| 5,851,315 A | 12/1998 | Strathearn et al. | 250/303 |
| 5,856,018 A | 1/1999 | Chen et al. | 427/162 |
| 5,858,198 A | 1/1999 | Florio et al. | 205/122 |
| 5,869,140 A | 2/1999 | Blohowiak et al. | 134/28 |
| 5,871,625 A | 2/1999 | Leddy et al. | 106/316 |
| 5,905,336 A | 5/1999 | Van Hal et al. | 427/226 |
| 5,938,604 A | 8/1999 | Wagner et al. | 600/436 |
| 6,059,752 A | 5/2000 | Segal | 604/107 |
| 6,077,413 A * | 6/2000 | Hafeli et al. | 205/170 |

FOREIGN PATENT DOCUMENTS

| | | |
|---|---|---|
| WO | WO 95/19807 | 7/1995 |
| WO | WO 97/19723 | 6/1997 |
| WO | WO 98/12979 | 4/1998 |
| WO | WO 98/48851 | 11/1998 |
| WO | WO 00/29501 | 5/2000 |

OTHER PUBLICATIONS

Gruberger, J., et al., "Sulfate Solution for Deposition of Ni–Cr–P Amorphous Alloys", Surface and Coatings Technology, 53(1992) 203–213, no month.

Hafeli, Urs. O., et al., "Electrodeposition of Radioactive Rhenium onto Stents to Prevent Restonosis", Biomaterials 19 (1998) 925–933, no month.

Haseb, A.S.M.A., et al., "XRD, XPS and SIMS Investigations on Electrodeposited Nickel–Phosphorous Alloy Coatings", Thin Solid Films 283 (1996) 140–144. No month.

Lakeman, Charles D.E., et al., "Sol–gel Processing of Electrical and Magnetic Ceramics", Materials Chemistry and Physics, 38 (1994) 305–324. No month.

Nazeri, Asar et al., "Ceramic Composites by the Sol–Gel Method: A Review", Ceram. Eng. Sci. Proc. 14[11–12] pp. 1–19 (1993). No month.

O'Donoghue, J.A. et al., "Relationships between Tumor Size and Curability for Uniformly Targeted Therapy with Beta–Emitting Radionuclides", The Journal of Nuclear Medicine, vol. 36, No. 10, Oct., 1995, pp. 1902–1909.

Ohno, Izumi, "Electrochemistry of Electroless Plating", Materials Science and Engineering, A146 (1991) 33–49. No month.

Steinhauser, S., et al., "Composite Coatings: Manufacture, Properties, and Applications", The Institute of Materials, Surface Engineering, 1997, vol. 13, No. 4. pp. 289–294. No month.

Tracy, Robert P., et al., "Practical Guide to Using Ni–P Electroless Nickel Coatings", Materials Selection and Design, Jul. 1990, pp. 65–70.

Weil, R., et al., "Comparison of Some Mechanical and Corrosion Properties of Electroless and Electroplated Nickel–Phosphorous Alloys", Plating and Surface Finishing, Feb. 1989, pp. 62–66.

Yamaguchi, K., et al., "Magnetic Properties of Iron–Boron–Oxide and Iron–Phosphor–Oxide Glasses Prepared by Sol–Gel Method", IEEE Transactions on Magnetics, vol. 25, No. 5, Sep. 1989, pp. 3321–3323.

Ying, Wei–chi et al., "Removal of Nickel and Phosphorus from Electroless Nickel Plating Baths", Metal Finishing, Dec. 1987, pp. 23–31.

* cited by examiner

RADIOACTIVE COATING SOLUTIONS METHODS, AND SUBSTRATES

This application claims the benefit under 35 U.S.C. §119(e) of Provisional Applications Serial Nos. 60/108, 963, filed Nov. 18, 1998, and Ser. No. 60/141,766, filed Jun. 30, 1999, the entire contents of each of which are hereby incorporated by reference.

BACKGROUND OF THE INVENTION

1. Field of the Invention

The present invention relates to radioactive coating solutions, radioactive sols and sol-gels, methods used to form radioactive coatings on a variety of substrates, and to radioactive coated substrates. In particular, the present invention relates to a medical device, or a component thereof, having at least one radioactive coating layer thereon.

2. Description of Related Art

Metal coatings are used in a variety of industrial and engineering applications to provide, for example, resistance to corrosion and wear, enhanced lubricity and decorative appearance. Several methods are used to form metal coatings, including electrodeposition and electroless deposition. Electrodeposition depends on the use of applied voltage to produce metal deposition, while electroless deposition depends on chemical reactions (including the chemical reduction of a metal) independent of applied voltage. See, e.g., Dini, J. W., Developments and Trends in Electrodeposition, SAMPE Quarterly (1989) 28–32; and Ohno, I. Electrochemistry of Electroless Plating, Materials Science and Engineering, vol. A146 (1991) 33–49.

A wide variety of solutions for electrodeposition and electroless deposition are known, as theoretically any element or combination of elements, including metals and non-metals, can be added to a carrier metal to provide a suitable coating solution, wherein the carrier metal is present as an ion. In particular, metalloids including phosphorus and boron can be added to a carrier metal to provide a coating solution. Commonly used carrier metals include nickel, copper, cobalt, platinum, palladium, chromium, gold and silver. Particularly common are nickel and nickel alloy coating solutions, including nickel-phosphorus, nickel-boron, palladium-nickel, nickel-chromium, nickel-cobalt, nickel-phosphorus-boron, and copper-nickel chromium. Solutions are typically aqueous.

Electroless coatings are significantly more uniformly deposited than electrodeposited coatings, and are particularly desirable for coating complex shapes, including tubes and large components. Electroless deposition of nickel-phosphorus coatings, in particular, is well known. In general, electroless nickel phosphorus (ENP) coatings are dense, non-porous metal glass structures resembling polished stainless steel. ENP coatings typically contain between 3 and 13% by weight phosphorus, with the percentage significantly influencing both the chemical and physical properties of the coating. High phosphorus ENP coatings provide superior corrosion protection and are generally more continuous that lower phosphorus ENP coatings. R. P. Tracey, Practical Guide to Using N-P Electroless Nickel Coatings, Materials Selection and Design, 1990. ENP coatings are generally highly adhesive, providing resistance to chipping and peeling under extreme conditions. Electroless coatings may be amorphous or crystalline in structure Materials to be coated by electroless deposition are commonly metal. Electroless coatings can be applied to most metals and alloys, including steel and stainless steel, iron, aluminum, titanium, magnesium, copper, brass, bronze and nickel. In some cases, in addition to cleaning and removing surface oxides, the metal or alloy must be pre-treated to provide a catalytic surface for the electroless coating. For example, for coating Elgiloy™ with ENP, the surface must be coated (i.e., by electrodeposition or electroless deposition) with Ni prior to being coated with ENP. Electroless deposition may also be used to coat a variety of materials that are generally non-conductive, including plastics, glasses and ceramics, and composite materials. Coating of polymers genereally requires additional steps to activate the polymer surfaces. A variety of processes are known for making polymer surfaces catalytic to the coating process. A tin-palladium catalyst, for example, can be absorbed onto the surface of the substrate, or applied as a catalytic coating.

Electroless deposition is carried out by immersing the substrate to be coated in an coating solution or bath comprising a carrier metal ion and a reducing agent. In ENP coating solutions, the most common reducing agent is hypophosphite ion ($H_2PO_2^-$). (Tracey, 1990). The metal ions are chemically reduced in the presence of the reducing agent and deposited onto the substrate surface. Deposition rates are typically 10–20 microns per hour. Typical commercial ENP coating are from about 2.5 to about 125 microns thick. (Tracey, 1990). Thicker coatings are typically required for rough surfaces.

Metal coatings may also be formed by electrodeposition. For example, nickel-phosphorous coatings may be produced by electrodeposition, and have comparable properties to those prepared via electroless deposition. Weil et al., Comparison of Some Mechanical and Corrosion Properties of Electroless and Electroplated Nickel-Phosphorous Alloys, Plating and Surface Finishing (Feb. 1989) 62–66.

Materials to be coated by electrodeposition include most metals and alloys, which in some cases must be clean and oxide free to provide a catalytic surface for electrodeposition. In certain circumstances, polymers may also be coated by electrodeposition. For example, plastics incorporating conductive particles can be coated by electrodeposition. Intrinsically conductive polymers may also be coated by electrodeposition. Generally, electrodeposition rates of Ni—P are higher than normally obtained via electroless methods. Also, electroplating solutions are more stable and have fewer replenishment problems. However, electrodeposited Ni—P does not coat complicated shapes with as uniform a thickness as ENP.

Electrodeposition is carried out by immersing the substrate to be coated in a coating solution or bath comprising a carrier metal ion and a radioisotope. Unlike electroless deposition, electrodeposition requires an applied current. In general, a reducing agent such as is necessary for electroless deposition is not required for electrodeposition, although reducing agents are not uncommonly present for electrodeposited Ni—P coatings, for example.

Methods for producing radioactive metal articles are also known. For example, it is known to manufacture a metal article comprising a radioisotope, e.g., by alloying the radioisotope with a metal or alloy or by ion implantation with a radioactive element It is also known to manufacture non-radioactive metal articles which are subsequently made radioactive, e.g., by neutron bombardment. Each method of preparing radioactive metal articles, however, is associated with particular disadvantages. Manufacture of alloys using radioactive elements, for example, is problematic because many of the most desirable radioisotopes (e.g., P) show limited solubility as equilibrium alloying ingredients. Moreover, health physics safety issues associated with the manufacture of various articles effectively prohibit certain methods of manufacture.

The use of neutron bombardment to produce radioactive metal articles is similarly problematic, given limited access to nuclear reactors and tremendous costs. Neutron bombardment also constrains the size of components which can be irradiated. Moreover, neutron bombardment activates all components of the metal article that are susceptible to neutron activation, so that undesirable and potentially dangerous radioisotopes may be generated. Many standard alloy components, including Fe and Cr, form undesirable radiation reaction products. Thus, metals and alloys subject to neutron bombardment must be extremely pure and free of problematic elements, e.g., Na.

It is one object of the present invention to provide a radioactive coating that can be produced from less than extremely pure materials, and without placing the coated article into a nuclear reactor.

It is a further object of the present invention to provide a radioactive coating comprising any of a wide variety of radioisotopes, including insoluble radioisotopes.

It is another object of the present invention to provide a radioactive coating solution which permits separation of the radioisotope therefrom.

It is yet another object of the present invention to provide a method of making a substrate radioactive by applying one or more radioactive coating layers thereto.

It is another object of the present invention to provide radioactive coated substrates.

It is a further object of the present invention to provide substrates coated with multiple layers of radioactive coatings.

It is yet a further object of the present invention to provide a medical device, or a component of a medical device, coated with one or more radioactive coating layers.

It is a still further object of the present invention to provide a catheter having an component coated with one or more radioactive coatings layers, and more particularly, an expandable component coated with one or more radioactive coating layers.

It is still a further object of the present invention to provide a method of making a substrate having a variable radioactive coating or coatings capable of producing an asymetric radiation field.

It is yet a further object of the present invention to provide a substrate having a variable radioactive coating or coatings capable of producing an asymetric radioactive field.

It is an object of the present invention to provide a brachytherapy device coated with a variable radioactive coating or coatings capable of producing an asymetric radioactive field.

It is a further object of the present invention to provide a method of producing a radiation field corresponding to a target field.

It is a still further object of the present invention to provide a method of producing a radiation field corresponding to the morphology of a tumor.

SUMMARY OF THE INVENTION

The invention disclosed herein relates to radioactive coating solutions, radioactive sols and sol-gels, methods used to form a radioactive coatings on a substrate, and to radioactive coated substrates.

The present invention relates to a coating solution comprising, in solution, at least one carrier metal ion and a radioisotope. In a particular embodiment of the present invention, the coating solution further comprises a reducing agent. The radioisotope present in the coating solution may be soluble or insoluble or present as the insoluble compound of a radioisotope.

The present invention also relates to a method of making a substrate radioactive by applying a radioactive coating solution to the substrate to form a substrate having a radioactive coating formed thereon. In a particular embodiment of the method, the radioactive coating is a radioactive composite coating comprising a metal matrix and a radioactive dispersed phase. Methods of applying the radioactive coating solution to the substrate include electrodeposition and electroless deposition.

The present invention also relates a radioactive sols and radioactive sol-gels. The radioactive sol of the present invention comprises a metal alkoxide or other organometallic compound and a radioisotope. In a particular embodiment, the radioisotope is insoluble or the insoluble compound of a radioisotope, and is either added to the metal alkoxide or other organometallic compound prior to polymerization, or added by impregnation after partial polymerization. The present invention also relates to methods of making a substrate radioactive by applying a radioactive sol or sol-gel to a substrate to form a radioactive coating. In a particular embodiment of the present invention, the radioactive coating is a composite coating comprising an oxide matrix and a radioactive dispersed phase. Methods of applying the radioactive sol or sol-gel to the substrate include, without limitation, spin coating and dip coating.

The present invention further relates to methods of forming multiple radioactive coating layers on a substrate. Optionally, the method includes deposition of an activation layer over the substrate prior to deposition of the radioactive coating layer, such that the activation is interposed between the substrate and the radiation coating layer. In a particular embodiment, the method includes deposition of an activation layer between two radioactive coatings layers. Optionally, the method also includes deposition of a protective coating layer over the radioactive coating.

The present invention also relates to radioactively coated substrates. Suitable substrates include, but are not limited to, metals, alloys, polymers, plastics, ceramics and composites. In a particular embodiment of the present invention, the substrate is a medical device formed from such materials, or a component thereof. Representative medical devices include catheters, guidewires, stents, and brachytherapy devices. More particularly, the substrate is be a catheter component, and more particularly, the expandable component of a catheter.

The present invention also relates to a method of making a substrate having a variable radioactive coating capable of producing an asymetric radiation field, as well as to substrates having a variable radioactive coating. In a particular embodiment, the present invention relates to a brachytherapy device having a variable radioactive coating capable of producing an asymetric radiation field.

The present invention also relates to a method of producing a radiation field corresponding to a target field. In particular, the method of the present invention involves the design or selection of a brachytherapy device having a variable radioactive coating capable of producing an asymetric radiation field, which can be used alone or in combination with other such devices to produce a radiation field that closely corresponds to the morphology of a tumor.

The present invention advantageously permits production of radioactive substrates by virtue of a radioactive coating or coatings applied thereto. The present invention overcomes limitations of the traditional alloying and nuclear bombardment methods used to render metal articles radioactive to provide a radioactive metal coating which can be formed from a wide array of radioisotopes, including insoluble radioisotopes, relatively safely and inexpensively.

In particular embodiments, the present invention advantageously permits separation of a radioisotope from a radioactive coating bath, reducing the volume of the coating solution which must be treated or disposed of as radioactive waste. This feature of the present invention also permits recharging of the radioisotope, providing a further economic benefit.

In certain other embodiments, the present invention advantageously permits production of a radioactive coated brachytherapy device which can be used alone or in combination with other such devices to produce a radiation field closely corresponding to the morphology of a tumor, reducing radiation damage to adjacent normal tissue. Thus, the dose of radiation that can be given to a tumor is increased with less damage to the adjacent normal tissue than is seen with radiation doses currently in use. This will most likely result in a higher response rate of tumors to brachytherapy, and in many cases, higher patient survival rates.

These and other advantages of the present invention will be apparent to those skilled in the art in view of the disclosure set forth below.

DETAILED DESCRIPTION OF SPECIFIC EMBODIMENTS

Figure 1:
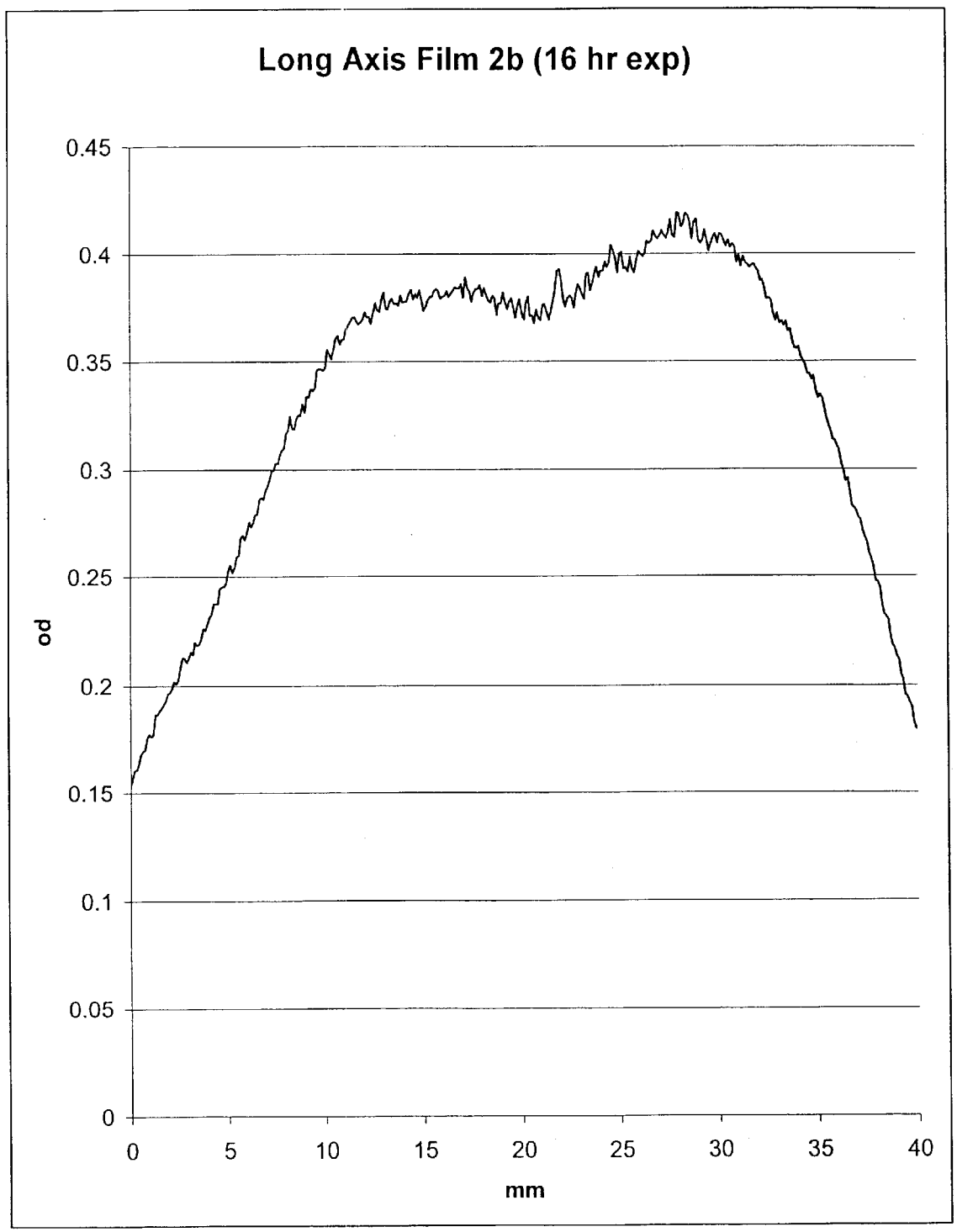
FIG. 1: depicts an isodensity curve of the radioactive coating applied to a catheter according to Example 1, as measured along the catheter's long axis, illustrating uniformity of deposition.

The invention disclosed herein relates to radioactive coating solutions, radioactive sols and sol-gels, methods used to form a radioactive coatings on a substrate, and to radioactive coated substrates.

The present invention relates to a radioactive coating solution comprising at least one carrier metal ion and a radioisotope. In a particular embodiment, the radioactive coating solution comprises a carrier metal ion, a radioisotope and a reducing agent. Suitable carrier metals ions include, without limitation, nickel, copper, cobalt, palladium, platinum, chromium, gold and silver ions. In one embodiment of the present invention, the carrier metal ion is nickel ion. The concentration of carrier metal ion in the radioactive coating solution may vary, as would be understood by one skilled in the art. A representative carrier metal ion concentration is from about 1 to about 30 g/L. Carrier metal ion concentrations from about 3 to about 15 g/L are particularly suitable for use with radioactive coating solutions wherein the carrier metal ion is nickel.

Radioisotopes suitable for use in the coating solution of the present invention include beta, gamma, or alpha emitters. In a particular embodiment, the radioisotope is a non-metal (e.g., $^{32}P$). Beta radiation penetrates only a limited distance through human tissue, and is therefore particularly desirable for localized radiation therapy. Beta emitters suitable for use in the present invention include, but are not limited to, $^{14}C$, $^{35}S$, $^{45}Ca$, $^{90}Sr$, $^{89}Sr$, $^{32}P$, $^{33}P$, $^{3}H$, $^{77}As$, $^{111}Ag$, $^{67}Cu$, $^{166}Ho$, $^{199}Au$, $^{198}Au$, $^{90}Y$, $^{121}Sn$, $^{148}Pm$, $^{149}Pm$, $^{176}Lu$, $^{17}Lu$, $^{106}Rh$, $^{47}Sc$, $^{105}Rh$, $^{131}I$, $^{149}Sm$, $^{153}Sm$, $^{156}Sm$, $^{186}Re$, $^{188}Re$, $^{109}Pd$, $^{165}Dy$, $^{142}Pr$, $^{143}Pr$, $^{144}Pr$, $^{159}Gd$, $^{153}Gd$, $^{175}Yb$, $^{169}Er$, $^{51}Cr$, $^{141}Ce$, $^{147}Nd$, $^{152}Eu$, $^{157}Tb$, $^{170}Tm$, and $^{194}Ir$. In a particular embodiment, the radioisotope is $^{32}P$.

Gamma emitters suitable for use in the present invention include, but are not limited to, the group comprising $^{137}Cs$, $^{60}Co$ and $^{192}Ir$. Similarly, suitable alpha emitters include, but are not limited to, the group comprising $^{226}Ra$ and $^{222}Rn$ Other radioisotopes suitable for use in the present invention include, but are not limited to, $^{125}I$, $^{192}Ir$ and $^{103}Pd$.

In a particular embodiment, the coating solution of the present invention is prepared by adding a water-soluble phosphorus compound to the coating solution, wherein at least a fraction of the P is $^{32}P$. Put another way, $^{32}P$ is present in the coating solution as an aqueous solution of phosphorous-containing ions. In a particular embodiment, the source of $^{32}P$ is any compound containing hypophosphite ($H_2PO_2^-$). Non-limiting examples of hypophosphite compounds suitable for use in the present invention include hypophosphorus acid, sodium hypophosphite, ammonium hypophosphite, potassium hypophosphite and lithium hypophosphite. In a particular embodiment, aqueous $NaH_2PO_2.H_2O$ or $NaH_2PO_4.2H_2O$ is added to the coating solution, wherein at least a fraction of the P is in the form of $^{32}P$.

In a further embodiment of the present invention, the source of $^{32}P$ is any compound containing phosphite ($HPO_3^{2-}$). Phosphorous acid, $H_3PO_3$, provides a non-limiting example of a phosphite material suitable for use in the present invention. In a still further embodiment of the present invention, the source of $^{32}P$ is any compound containing orthophosphate ($PO_4^{3-}$). Orthophosphoric acid, $H_3PO_4$, provides a non-limiting example of an orthophosphate compound suitable for use in the present invention.

The amount of radioisotope present in the radioactive coating solution may vary, as would be understood by one skilled in the art. A representative specific activity is from about 0.1 to about 5000 Ci/g, and more particularly, about 20 Ci/g (or 64/Ci/mole) which amount is particularly suitable for coating solutions comprising $^{32}$P in the form of hypophosphite or hypophosphorus acid. This representative specific activity falls below the theoretical maximum for $^{32}$P (i.e., slightly greater than 9000 Ci/mmol, or 9,000,000 Ci/mol). This representative amount is particularly suitable where $NaH_2PO_2 \cdot H_2O$ is the only reductant present in an electroless Ni—P coating solution.

Suitable reducing agents for use in the coating solution of the present invention include, but are not limited to, hypophosphites, formaldehyde, borohydride, dialkylarnine boranes (e.g., dimethyl borane), and hydrazine. Each of these reductants has a particular condition range that is well known to one skilled in the art. In particular, for ENP, $NaH_2PO_2$ is commonly used as a reductant, with a representative a range from about 5 g/l to about 50 g/l.

As would be evident to one skilled in the art, the radioisotope of the coating solution may be the radioactive form of an element present as a the reducing agent, or component thereof. For example, in a given coating solution, the radioisotope may be $^{32}$P while the reducing agent might be $NaH_2PO_2$. Alternatively, the radioisotope may be the radioactive form of the carrier metal. For example, in a given coating solution, the radioisotope may be $^{198}$Au, while the carrier metal is also Au.

In a particular embodiment of the present invention, the coating solution comprises $NiSO_4$ (26 g/l), $NaH_2PO_2 \cdot H_2O$ (26 g/l), Na-acetate (34 g/l), and malic acid (21 g/l), wherein at least a fraction of the P is $^{32}$P. In a further embodiment of the present invention, the coating solution comprises AuCN (2 g/L), $NaH_2PO_2$ (10 g/L), KCN (0.2 g/L), wherein at least a fraction of the P is $^{32}$P. In a still further embodiment, the coating solution comprises AuCN (2 g/L), $NaH_2PO_2$ (10 g/L), KCN (0.2 g/L) wherein at least a fraction of the Au is $^{198}$Au. In a still further embodiment, the coating solution comprises AuKCN (5.8 g/L), KCN (14 g/L), KOH (11.2 g/L), and KBH4 (21.6 g/L), wherein at least a fraction of the Au is $^{198}$Au.

Additional components may be added to the coating solution to vary the physical and chemical characteristics of the coating. For example, the solution may comprise $NiSO_4$, NiCl, $NaH_2PO_2$ and $H_3PO_4$, wherein at least a fraction of the P is $^{32}$P.

The present invention further relates to a method of forming a radioactive coating on a substrate, which coating comprises at least one carrier metal and a radioisotope. The coating is formed by contacting the substrate with a radioactive coating solution comprising a carrier metal ion and a radioisotope. The coating solution may have the properties described above, as one skilled in the art would appreciate. Various coating techniques known in the art are suitable for use in the present invention including, but not limited to, electroless deposition, electrodeposition, chemical vapor deposition, physical deposition, thermal spraying, sol-gel methods, or any combination thereof. Certain methods may be more suitable for certain substrates, as would be understood by one skilled in the art.

Substrates coated according to the present invention may include, but are not limited to, metals, alloys, polymers, plastics, ceramics and composites. In a particular embodiment, the substrate is medical device, such as a catheter, guidewire, stent or brachtherapy device (i.e., a hollow or solid needle), or a component thereof. In a more particular embodiment, the substrate is an expandable component of a catheter. This expandable component may be formed from a metal, alloy, polymer, plastic, ceramic or composite. In a particular embodiment, the expandable component is formed from an alloy, such as Elgiloy™.

In a particular embodiment of the method, electroless deposition is used to form a radioactive coating on a substrate. In this embodiment, the substrate is contacted with the radioactive coating solution, for a time, at a concentration, a temperature and pH sufficient to chemically deposit a radioactive metal coating on the substrate. It may be necessary to clean the substrate and to remove surface oxides therefrom prior to deposition of the radioactive coating. It may further be necessary to coat the substrate with a catalytic coating or activating layer prior to electroless deposition of the radioactive coating, as would be recognized by one skilled in the art. The catalytic coating may be a non-radioactive Ni coating, for example. Suitable electroless coating solutions include, without limitation, electroless nickel coating solutions comprising hypophosphite, wherein at least a fraction of the P in hypophosphite is $^{32}$P. Typical electroless nickel coating solutions are reviewed in W.

Ying and R. Bank, Metal Finishing (December 1987), pp. 23–31, and in W. Riedel, Electroless Nickel Plating, ASM International (1991), pp.9–32, which are incorporated herein by reference. Suitable electroless coating solutions also include electroless gold coating solutions comprising hypophosphite, wherein at least a fraction of the P in the hypophosphite is $^{32}$P, as well as electroless gold solutions wherein at least a fraction of the Au is present as $^{198}$Au. In a particular embodiment of the method, the radioisotope is the radioactive form of an element present as the reducing agent, or a component thereof (e.g., the radioisotope is $^{32}$P, and the reducing agent is $Na_2H_2PO_2$). In a further embodiment of the method, the radioisotope is the radioactive form of the carrier metal (e.g., the radioisotope is $^{198}$Au, while the carrier metal is Au.)

Conditions for electroless deposition of a particular coating solution can vary, as would be recognized by one skilled in the art. These conditions also vary depending on the desired coating composition. Representative condition ranges include: (1) a pH range of from about 4.5 to about 10.0, and more particularly 4.8; (2) a temperature range of from about 60 to about 100° C., and more particularly 88° C.; (3) a metal concentration range from about 3 to about 15 g/L; (4) a deposition rate range of from about 0.5 to about 257 mil/hour, and more particularly 10 mil/hour; (5) a bath loading range of from about 0.1 to about 1.0 square feet per gallon, and more particularly 0.6 square feet per gallon; and (6) one or more reductants, from about 5 to about 50 g/L. A representative deposition of 1 $\mu$M at 10 $\mu$M/hour would take 6 minutes. These representative ranges are particularly suitable for use in electroless deposition of an electroless nickel-phosphorus coating solution having $Na_2PO_2$—$H_2O$ as a reductant, wherein at least a portion of P is $^{32}$P. Other suitable conditions for electroless nickel-Phosphorus deposition are reviewed in Hur et al, Microstructures and crystallization of electroless Ni—P deposits, *Journal of Materials Science*, Vol 25, (1990), 2573–2584, which is incorporated herein by reference. Accurate temperature and metal concentration control are important to achieve uniform deposition rates. Various coating thickness' are achievable, as would be apparent to one skilled in the art. A representative coating thickness ranges from about 0.1 to about 20 $\mu$m, and typically about 1.0 to about 2.0 $\mu$m. Optionally, a sealing or protective layer may be formed over the radioactive coated substrate (i.e., a non-radioactive Ni sealing layer).

Figure 8A:
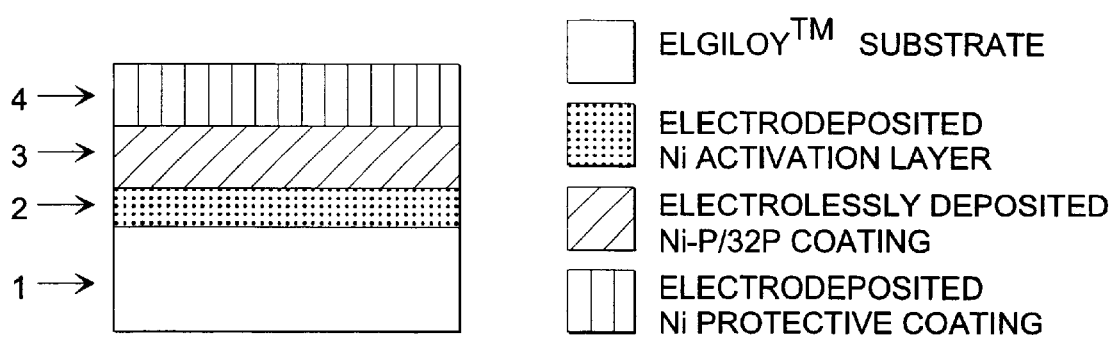
FIG. 8: depicts substrates having a radioactive coating or coatings formed thereon.

FIG. 8A depicts a substrate having an electroless radioactive coating. More particularly, FIG. 8 depicts an Elgiloy substrate (1) coated by electrodeposition of a Ni activiation layer (2), which activated substrate has a radioactive Ni—P/$^{32}$P layer (3) formed thereon. The radioactive coated substrate in FIG. 8 also has a Ni sealing layer electrodeposited thereon (4).

The method of the present invention also includes the use of electrodeposition to apply a radioactive coating on a substrate. According to this method, the substrate is contacted with a radioactive coating solution for a time, at a concentration, at a temperature and voltage sufficient to electrically deposit a radioactive metal coating on the substrate. In some cases, it may be necessary to clean the substrate surface and to remove surface oxides prior to coating. In a particular embodiment of the method, the radioisotope present in the coating solution is a non-metal (e.g., $^{32}$P). In a more particular embodiment, the coating solution comprises hypophosphite, phosphite, and/or orthophosphate, wherein at least a fraction of the P in the hypophosphite and/or the phosphite, and/or the orthophosphate is $^{32}$P.

Suitable coating solutions for use an electrodeposition of radioactive metal coatings include, without limitation, a solution comprising nickel sulfate (150 g/L), nickel chloride (45 g/L), sodium hypophosphite (100 g/L), and orthophosphoric acid (50 g/L), wherein at least a portion of the P present is $^{32}$P. Though conditions for electrodeposition vary, as would be familiar to those skilled in the art, representative conditions for electrodeposition of this radioactive coating solution include (1) a pH of about 6.0 to about 7.0; (2) a temperature of about 55–60° C.; (c) a coating density from about 20 mA/cm$^2$ to about 500 mA/cm$^2$, and more particularly, about 80 mA/cm$^2$. In one embodiment, the method yields a dense, amorphous Ni—P coating, at a coating rate of 4.2 $\mu$m/h. Generally, for electrodeposited coatings, coating rates may vary considerably from, for example, about 0.1 to about 25 $\mu$m/hour using conventional electrodeposition. Various coating thickness' are achievable, as would be apparent to one skilled in the art. A representative coating thickness ranges from about 0.1 to about 20 $\mu$m, and typically about 1.0 to about 2.0 $\mu$m. Optionally, a protective or sealing layer is formed onto the radioactive coated substrate, such as a non-radioactive Ni coating.

In a further embodiment, a radioactive coating solution suitable for electrodeposition comprises CrK(SO$_4$)$_2$.12H$_2$O (100 g/L), NiSO$_4$.6H$_2$O (50 g/L), (NH$_4$)$_2$SO$_4$ (50 g/L), NaH$_2$PO$_2$.H$_2$O (50 g/L), Na$_3$C$_6$H$_5$O$_7$.2H$_2$O (50 g/L), C$_6$H$_8$O$_7$ (25 g/L), H$_3$BO$_3$ (20 g/L), (NH$_2$)$_2$CS (0.01 g/L), C$_{10}$H$_{16}$O (0.333 g/L), and C$_{12}$H$_{25}$SO$_4$Na (0.1 g/L), wherein at least a fraction of the P in NaH$_2$PO$_2$.H$_2$O is present as $^{32}$P. Representative condition for electrodeposition of this solution include (1) pH from about 2 to about 4, and typically 2.3; (2) current density from about 5 to about 400 mA/cm2, and typically about 200 mA/cm2; (3) a temperature at or about room temperature.

The method of the present invention also includes the use of an applicator to apply a radioactive coating solution to the substrate. Suitable applicators include, but are not limited to, brushes and pens. Applicators for use in electroplating have an electrically conductive component. See U.S. Pat. No. 5,401,369 and U.S. Pat. No. 4,159,934.

In a particular embodiment of the present invention, the radioactive coating solution comprises at least one carrier metal ion and either an insoluble radioisotope or the insoluble compound of a radioisotope. In a particular embodiment, the radioactive solution also includes a reducing agent, with suitable reducing agents including identified above for radioactive coating solutions comprising at least one dissolved carrier metal ion and a dissolved radioisotope. The carrier metal ion is dissolved in solution, and may be, without limitation, nickel, copper, chromium, cobalt, platinum, palladium, gold or silver ion. In a particular embodiment, the carrier metal ion is copper, which can be dissolved in the coating solution in the form of any soluble copper salt, such as CuSO$_4$. In a further embodiment, the dissolved carrier metal ion is nickel.

The concentration of carrier metal ion in the radioactive coating solution may vary, as would be understood by one skilled in the art. A representative carrier metal ion concentration range would be from about 1 to about 30 g/L. Carrier metal concentrations from about 3 to about 15 g/L are particularly suitable for use with radioactive coating solutions wherein the carrier metal is nickel.

The insoluble radioisotope may comprise an insoluble radioisotope or insoluble compound of a radioisotope, such as an insoluble metal salt or oxide. Insoluble radioisotopes suitable for use in the coating solution of the present invention include, without limitation, insoluble $^{32}$P, $^{90}$Y and $^{198}$Au. Insoluble compounds of radioisotopes include, without limitation, FeP, NiP, CoP, SnP, Ti$_4$P3 and Y$_2$O$_3$, wherein $^{32}$P, $^{121}$Sn or $_{90}$Y are present in substantial amounts. Alternatively, the soluble compound of a radioisotope can be rendered insoluble, e.g., by encapsulation or immobilization in an insoluble coating or matrix. Various other metal oxides and metal phosphides are also suitable for use in the present invention.

The insoluble radioisotopes or insoluble compounds of radioisotopes may be in the form of metal or alloy particles, metal oxide particles, or polymeric particles. The size of the particles present in the coating solution may vary, as would be apparent to one skilled in the art. A representative particle size ranges from about 5 nm to about 30 $\mu$m. As a non-limiting example, $^{198}$Au particles formed by wet grinding gold range from about 1 to about 10 $\mu$m in diameter are suitable for use in the present invention. In a particular embodiment of the present invention, the radioactive coating solution comprises particles of varying sizes. See U.S. Pat. No. 4,547,407.

The amount of insoluble radioisotope present in the radioactive coating solution may vary, as would be understood by one skilled in the art. A representative amount has a specific activity of about 0.1 to about 5000 Ci/g.

In a particular embodiment of the present invention, the coating solution comprises 1.0 mol/L CuSO$_4$, 0.75 mol/L H$_2$SO$_4$, and 35 mg/L P in particulate form, suspended in solution via agitation, wherein at least a fraction of the P is $^{32}$P. In a further embodiment of the present invention, the coating solution comprises NiSO$_4$(26 g/L), NaH$_2$PO$_2$—H$_2$O (26 g/L), Na-acetate (34 g/L), lactic acid (18 g/L), malic acid (21 g/L), and Au in particulate form, wherein at least a portion of the Au is $^{198}$Au. Additional components may be added to the coating solution to vary the physical and chemical characteristics of the coating solution.

The present invention also relates to a method of forming a radioactive coating a substrate, which coating comprises a metal matrix and a dispersed radioactive phase. The composite coating is formed by contacting the substrate with a radioactive coating solution comprising at least one carrier metal and either an insoluble radioisotope or an insoluble compound of a radioisotope. The radioactive coating solution may have the properties described above, as one skilled in the art would appreciate. Suitable coating techniques include, but are not limited to, electroless deposition, electrodeposition, chemical vapor deposition, physical deposition, thermal spraying, or any combination thereof. Certain methods may be more suitable for certain substrates, as would be understood by one skilled in the art.

The quantity of radioactive particles deposited onto the substrate is influenced by various factors, including (1) the concentration of radioactive particles in the coating solution; (2) particle size and distribution; and (3) coating conditions. It is generally necessary to agitate the coating solution during the coating process. Substrates coated may include, but are not limited to, metals, alloys, polymers, ceramics and composites. In a particular embodiment, the substrate may be a medical device, or a component thereof, formed of metal, alloys, polymers, ceramics or composites, or combination thereof. Representative medical devices, without limitations, include catheters, guidewires, stents and brachytherapy devices. In a particular embodiment, the substrate is an expandable component of a catheter. In a particular embodiment, the expandable component is formed from an alloy, such as Elgiloy™.

In one embodiment of the method of the present invention, the radioactive composite coating is formed on the substrate by electrodeposition. The use of electrodeposition to form composite coatings is discussed in U.S. Pat. No. 5,266,181. More particularly, the substrate to be coated is contacted with the coating solution of the present invention for a time, at a concentration, a temperature, a cathode current density, and inter-electrode distance sufficient to electrically deposit a radioactive composite coating thereon. In some cases, it may be necessary to clean the substrate and to remove surface oxides therefrom prior to deposition of the radioactive coating. In a particular embodiment of the method of the present invention, the radioactive coating solution comprises 1.0 mol/L $CuSO_4$, 0.75 mol/L $H_2SO_4$, and a steady state concentration of 35 mg/L P in particulate form, suspended in solution via agitation, wherein at least a fraction of P is $^{32}P$ Electrodeposition conditions may vary from one coating system to another, as would be recognized by one skilled in the art. In a particular embodiment, electrodeposition of the Cu—P coating solution above is performed at a cathode current density of 18 $mA/cm^2$, an inter-electrode distance of 5 cm, at a temperature at or near 40° C. See J. W. Graydon and D. W. Kirk, "Suspension Codeposition in Electrowinning Cells: The Role of Hydrodynamics," the Canadian Journal of Chemical Engineering, vol, 69 (1991) 564–570. Agitation of the insoluble radioisotope particles is necessary via stirring or alternatively via recycle flows (500–1000 mL/min) to achieve uniform deposition rates. Coating rates vary with current density, temperature and other bath parameters. Suitable coating thickness' range from about 0.1 to about 20 $\mu$m, with about 5 $\mu$m generally suitable.

In a further embodiment of the present invention, the radioactive composite coating is formed by electroless deposition. Electroless deposition of composite coatings is reviewed in U.S. Pat. Nos. 5,232,744 and 5,389,229. More particularly, the substrate to be coated is contacted with the coating solution comprising at least one carrier metal ion, an insoluble radioisotope or insoluble compound of a radioisotope, and a reducing agent, for a time, at a concentration, at a temperature and pH sufficient to chemically deposit a radioactive composite coating thereon. Electroless deposition conditions may vary, as would be apparent to one skilled in the art. A representative electroless deposition involves contacting the substrate with a coating solution comprising from about 0.5 to about 0.5 mol of a metal, from about 0.1 to about 0.5 mol/l of a reducing agent and about 0.1 to about 500 g/l of particulate matter at least a fraction of which comprises a radioactive iosotope, wherein the coating solution has a pH ranging from about 4 to about 8, at a temperature of about 50 to about 95° C., and more particularly 70–90° C., for a time dependent on the particular coating thickness desiredIn this embodiment, the radioisotope present in the coating solution acts to reduce the metal present therein to deposit a metal layer on the substrate surface. Thickness of the coating may vary, and range from about 0.1 to about 20 $\mu$m, and typically from about 1 to about 2 $\mu$m. Optionally, the substrate to includes a catalytic coating layer or activating layer is coated onto the substrate prior to coating with the radioactive coating. The catalytic coating layer may be an electrolessly deposited or electrodeposited Ni coating layer, for example.

In one embodiment of the method of the present invention, the radioactive coating solution comprises $NiSO_4$ (26 g/L), $NaH_2PO_2$—$H_2O$ (26 g/L), Na-acetate (34 g/L), lactic acid (18 g/L), malic acid (21 g/L), and Au in particulate form, wherein at least a portion of Au is present as $^{198}Au$. In a further embodiment, the radioactive coating solution comprises $NiSO_4$ (26 g/L), $NaH_2PO_2$—$H_2O$ (26 g/L), Na-acetate (34 g/L), lactic acid (18 g/L), malic acid (21 g/L), and $Y_2O_3$ in particular form, wherein at least a fraction of the Y in $Y_2O_3$ is $^{90}Y$.

In a still further another embodiment, the coating solution comprises $NiSO_4$ (26 g/L), $NaH_2PO_2.H_2O$ (26 g/L), Na-acetate (34 g/L), lactic acid (18 g/L), malic acid (21 g/L), and a polymer phosphate in particulate form, wherein at least a fraction of the P in is $^{32}P$. Polymers containing phosphorus are reviewed in Nakano et al. (JP# 11061032). For example, Nakano describes preparation of a 2-hydroxyethyl metahacrylate/tert-Bu methacrylate/ethyl methacrylate phosphorylated with phosphorus oxychloride or polyphosphoric acid to form a polymer phosphate. In one embodiment of the present invention, a portion of the P in the phosphorus oxychioride or polyphosphoric acid is $^{32}P$, and the resulting radioactive polymer phosphate is powder processed to form a mean particle size ranging, for example, from about 5 to about 30 $\mu$m. The radioactive polymer particles are then be incorporated into the coating solution. All nonsoluble particles are kept in solution by means of intensive mechanical mixing (e.g., 300 rpm).

One advantage of the composite coating solution of the present invention is the ability to separate the radioactive source from the coating solution, e.g., by filtration. Separation makes it unnecessary to treat and dispose of the entire volume of the coating solution as radioactive waste, limiting the expense of waste treatment. According to this embodiment of the coating solution of the present invention, recharging of isotopes is permissible, providing an economic advantage.

The present invention also relates to radioactive sols and sol-gels, and to radioactive coatings formed via sol-gel techniques. The radioactive sol-gel of the present invention comprises an oxide and a radioisotope. Sol-gel techniques are reviewed generally in Pierre, A., Introduction to Sol-Gel Processing (1998), which is incorporated herein by reference. The radioactive sol-gel of the present invention may base formed via either colloidal or polymeric routes, resulting in either a polymeric or colloidal radioactive sol-gel. A discussion of polymeric and colloidal gels and synthesis routes is found in C. D. E. Lakeman and D. A. Payne, Invited Review: Sol-gel processing of Electrical and Magnetic Ceramics, Materials Chemistry and Physics, 38 (1994) 305–324, which is incorporated herein by reference.

Formation of both the colloidal and polymeric radioactive sol-gels of the present invention involves the dissolution of a metal ion, either as alkoxides or as other organometallic compound in a suitable solvent to form a fluid sol. The metal alkoxide or other organometallic compound hydrolyzes, either partially or completely, and then polymerizes, resulting in gelation and the formation of a radioactive semi-rigid gel, known as a sol gel. The radioisotope present in the sol may be either soluble or particulate (insoluble). The specific activity of this radioisotope ranges, for example, from about 0.1 to about 5000 Ci/g. Metal alkoxides suitable for use in the present invention include, but are not limited to, alkoxides of metals including silicon, boron, zirconium, titanium and aluminum. In particular, the metal alkoxide is silicon alkoxide.

In one embodiment of the present invention, a polymeric radioactive sol-gel is formed from a sol comprising a metal alkoxide and a radioisotope, which metal alkoxide hydrolyzes and then polymerizes to form a radioactive sol-gel. In a particular embodiment of the present invention, the radioactive sol-gel is formed by reacting orthophosphoric acid with silicon alkoxide, wherein at least a fraction of the P is $^{32}$P, to form a soluble, substantially linear polymer having P—O—Si linkages. This polymer is converted to a cross-linked polymer in the presence of sufficient water.

The radioactive sol-gel may also be formed via a colloidal route. Thus, in a particular embodiment, a Fe—P—O sol-gel may be formed according to the method described by Yamaguchi et al, in IEEE Transactions on Magnetics, 25 (1989) 3321–3323, incorporated herein by reference, wherein at least a portion of the P is $^{32}$P in the present invention.

In a particular embodiment, the radioisotope present in the sol-gel comprises an isoluble radioisotope or compound of a radioisotope. The formation of sol-gels comprising insoluble components is reviewed in Nazeri et al., Ceramic Composites by the Sol-Gel Method: A Review, Chemical Engin. Sci. Proc. 14[11–12] (1993), pp. 1–19, the contents of which are incorporated by reference. In a particular embodiment of the method, the sol comprises a metal alkoxide and an insoluble radioisotope, which metal alkoxide hydrolyzes, either partially or completely, and then polymerizes to from a radioactive sol-gel having insoluble radioisotope dispersed therein. In a further embodiment of the present invention, the sol comprises a metal alkoxide, which hydrolyzes and polymerizes to a state short of gelation, providing a partially polymerized sol which is then impregnated with the insoluble radioisotope. The impregnated sol then further polymerizes to produce a radioactive sol-gel having an insoluble radioisotope dispersed therein. In another embodiment of the present invention, a sol comprising a metal alkoxide is hydrolyzed and polymerized to form a sol-gel, which is then impregnated with the insoluble radioisotope to produce a radioactive sol-gel having insoluble radioisotope dispersed therein.

In a particular embodiment of the present invention, a sol is prepared by hydrolysis of tetra orthosilicate (TEOS) with radioactive particles (e.g., Au/$^{198}$Au) or p/$^{32}$P) mixed therein. The concentration of these particles may vary as would be recognized by those skilled in the art, with a representative activity from about 0.1 to about 5000 Ci/g.

The present invention also relates to methods of forming radioactive coatings onto substrates by so-gel techniques. In a particular embodiment of the method, the substrate to be coated is contacted with a radioactive sol comprising a metal alkoxide or an organometallic compound and a radioisotope. The sol hydrolyzes and polymerizes to produce a radioactive sol gel on the substrate. This radioactive sol-gel is then dried, and optionally subject to high temperature treatments that (a) may remove volatile species, including but not limited to hydroxyl groups or residual organic groups; and/or (b) result in processes which produce shrinkage and removal of residual porosity, including but not limited to sintering; and/or (3) result in processes that involve phase changes, including but not limited to crystallization and chemical reactions. The dried, and optionally high temperature treated, sol-gel forms a radioactive oxide coating comprising an oxide and a radioisotope. In a particular embodiment, the sol has undergone polymerization to a certain state, short of gelation, prior to being coated onto the substrate. Put another way, a partially polymerized sol is coated onto the substrate.

In a particular embodiment of the present invention, the substrate is contacted with a radioactive sol formed by reacting orthophosphoric acid with silicon alkoxide, wherein at least a fraction of the P in the orthophosphoric acid is $^{32}$P, as described above. Following hydrolysis and polymerization, a radioactive sol-gel is present on the article. The sol-gel is dried and optionally densified and crystallized to form a phosphorus silicon oxide coating containing $^{32}$P.

In another embodiment, a radioactive coating is formed by spin-coating a substrate with the radioactive Fe—P—O sol described above, where the sol has an appropriate viscosity (i.e., about 80 co). The radioactive coating is then dried in air at 200° C. Following drying, an optional heat treatment may be conducted to crystallize the gel into a polycrystalline ceramic coating. For example, heating for 24 hours at 600° C. crystallizes the coating.

The present invention also relates to a method of forming radioactive composite coating by sol-gel processes. In a particular embodiment of the method, a substrate is contacted with a radioactive sol comprising a metal alkoxide or another organometallic compound and an insoluble radioisotope. In a particular embodiment, the radioactive sol comprises hydrolyzed tetraethyl orthosilicate (TES) with $^{32}$P in particulate form dispersed therein, as described above. After the substrate is coated (i.e., by dipping or spin coating) with the sol containing a radioactive dispersed phase, it is dried to form a radioactive composite coating comprising an oxide matrix and a radioactive dispersed phase. The sol used to coat may or may not have undergone polymerization to a state short of gelation. Optionally, the radioactive coating is densified and crystallized into a crystalline ceramic article. During crystallization, the dispersed phase may optionally react/combine with the silica matrix, and consequently, the radioactive material may not appear to exist as a separate dispersed phase in the crystallized ceramic coating.

In a further embodiment of the method, a sol is formed comprising a metal alkoxide or another organometallic compound, and undergoes polymerization to a state short of gelation. An insoluble radioisotope is then introduced either into the partially polymerized sol, forming a radioactive partially polymerized sol which is then coated onto a substrate. In another embodiment of the present invention, a sol is formed comprising a metal alkoxide or another organometallic compound, and coated onto a substrate to form a sol-gel. This sol-gel is then impregnated with an insoluble radioisotope. Surface coating or full impregnation of the sol-gel can be achieved using this technique. The radioactive sol-gel is then dried and optionally crystallized into a crystalline ceramic structure.

The present invention is also directed to a method of forming multiple layers of a radioactive coating or coatings onto a substrate. Coating techniques suitable for forming such layers include, without limitation, electroless deposition, electrodeposition and sol-gel methods. According to one embodiment of the method, the substrate is contacted with a first radioactive coating solution under conditions sufficient to deposit a radioactive coating thereon. Optionally, the substrate is coated with a catalytic coating layer prior to deposition of the radioactive coating layer (i.e., a Ni activation coating layer). The substrate comprising a first radioactive coating is then contacted with one or more additional radioactive coatings solutions under conditions sufficient to deposit one or more additional radioactive coating layers thereon, thereby forming a substrate two or more radioactive coating layers. This process can be repeated to provide a substrate having multiple layers of radioactive coatings. Optionally, the coated substrate is rinsed prior to being contacted with the one or more additional radioactive coating solution, and/or between deposition of these additional radioactive coatings. Optionally, one or more catalytic/activation coating layers or activating layers may be coated onto the substrate and/or between one or more of the additional radioactive coating layers.

According to another embodiment of the present invention, the substrate is coated with a radioactive sol under conditions sufficient to deposit a radioactive sol-gel coating thereon. In a particular embodiment, the radioactive sol may be at least partially polymerized. The coated substrate is then coated with one or more additional radioactive sols under conditions sufficient to deposit a one or more additional radioactive sol-gel coatings thereon. This process can be repeated to provide a substrate having multiple layers of radioactive coatings.

The multiple radioactive coating layers of the present invention may be the same or different. For example, radioactive coating layers comprising soluble radioisotopes may be present or alternate with composite radioactive coating layers having a radioactive dispersed phase, while radioactive coating layers formed by electrodeposition may be present or alternate with radioactive coating layers formed by elctroless deposition or sol-gel processes, and variations thereof. The radioisotope and/or the carrier metal present in alternating radiaoctive coating layers may be the same or different. In one embodiment of the method, the first radioactive coating layer is different than one or more additional radioactive coatings layers. For example, the radioisotope of the first radioactive coating layer may be different than the radioisotope of one or more of the additional radioactive coatings layers. In a particular embodiment of the method, the radioisotope of the first coating layer is $^{198}$Au, while the radioisotope of one or more additional coating layers is $^{32}$P.

In one embodiment of the method of the present invention, an additional protective coating is formed over the radioactive coating or over the top radioactive coating where multiple radioactive coatings present in layers. This protective coating seals the radioactive coating and prevents dissolution of radioisotope in solution due to, for example, corrosion or abrasion. In a particular embodiment, the protective layer may formed by coating a Ni coating solution onto a radioactive coating by, for example, electrodeposition or electroless deposition. The protective layer, unlike the radioactive composite coating, does not contain radioisotope.

The invention disclosed herein also relates to radioactive coated substrates. Radioactive substrates have a variety of industrial and medical applications. It is known, for example, that radiation can be used to inhibit cell proliferation. Thus, radioactive substrates may be useful in treating a variety of diseases associated with aberrant cell proliferation, including cancer and arterial restenosis. One purpose of the present invention, therefore, is to provide radioactive substrates useful in the treatment of human disease. More specifically, a particular purpose of the present invention is to provide radioactive substrates useful in the treatment of cancer and vascular disease.

In one embodiment, the present invention relates to a coated substrate comprising at least a first layer of a radioactive coating disposed on a substrate material, wherein the radioactive coating comprises at least one carrier metal and a radioisotope. The carrier metal and radioisotope can be those carrier metals and radioisotopes identified herein for use in the radioactive coating solutions of the present invention, as would be understood by one skilled in the art. In a particular embodiment, the coating comprises Ni and phosphorus, wherein at least a fraction of the phosphorus is $^{32}$P. The coating may have a P content ranging, for example from low (1–4 weight % P) to medium (5–8 weight % P) to high (9–16 weight % P). In a particular embodiment, the fraction of P that is $^{32}$P is about 0.01% or less. Optionally, a catalytic coating layer or activation layer is also present, interposed between the substrate and the first layer of radioactive coating. For example, a non-radioactive Ni coating may be interposed between the substrate and the first radioactive coating layer.

In a further embodiment, the present invention relates to a coated substrate comprising at least a first layer of a radioactive composite coating comprising a metal matrix and a radioactive phase dispersed therein, disposed over a substrate material. The metal matrix may be formed of those metal identified herein for use in the radioactive coating solutions of the present invention, as would be understood by one skilled in the art. Similarly, the radioactive phase may be formed of those insoluble radioisotopes or insoluble compounds of radioisotopes identified herein for use in the radioactive coating solution of the present invention, as would be understood by one skilled in the art. Optionally, a catalytic coating layer (e.g., a non-radioactive Ni coating) is also present, interposed between the substrate and the first radioactive coating layer.

The present invention is also directed to substrates comprising multiple radioactive coating layers, which coating layers may be the same or different in composition or method of deposition, or both. Optionally, one or more catalytic coating layers may be interposed between one or more of the multiple radioactive coating layers. A activation or catalytic layer may also be formed onto the substrate prior to deposition of a radioactive coating layer thereon. In one embodiment of the present invention, the first layer of radioactive coating is different from at least one or more additional layers. For example, the radioisotope of the first layer is different from the radioisotope of at least one or more additional layers. In a particular embodiment, the radioisotope of one layer of radioactive coating is $^{198}$Au, while the radioisotope of one or more additional layers is $^{32}$P. Multiple radioactive coatings layers may be deposited by electrodeposition or electroless deposition, sol-gel methods, or a combination thereof. Suitable substrates include, but are not limited to, metals, alloys, polymers, plastics, ceramics and composites.

Figure 8B:
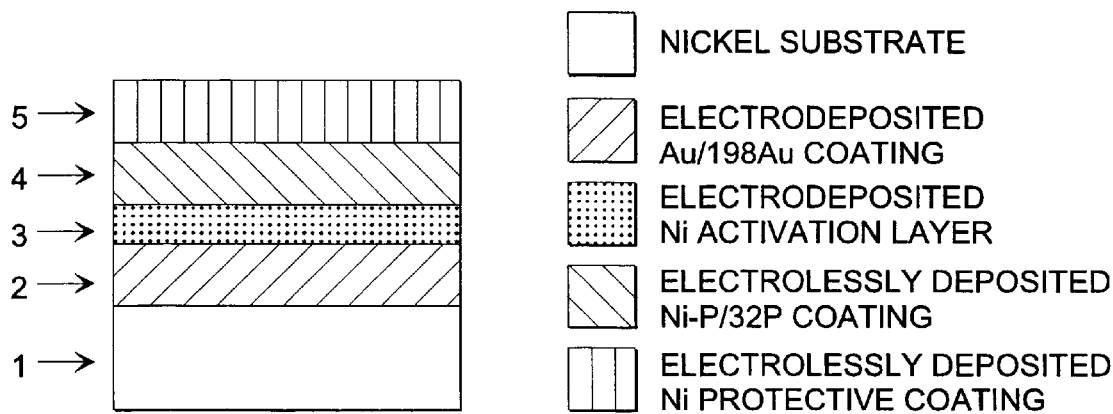

FIG. 8B depicts a substrate comprising multiple radioactive coating layers. A nickel substrate (1) is shown having an electrodeposited Au/$^{198}$Au layer (2) formed thereon. An electrodeposited Ni activation layer (3) if further formed on top of the Au/$^{198}$Au layer (2). Electrolessly deposited onto the Ni activation layer (3) is a Ni—P/$^{32}$P coating layer (4).

Finally, a protective coating (5) comprising Ni—P is formed by electroless deposition onto the coated substrate.

In a particular embodiment, the substrate of the present invention is a medical device formed from, for example, materials such as metals, alloys, polymers, ceramics or composites, or a combination thereof. Non-limiting examples of medical devices which are suitable substrates for the present invention include guidewires, stents and brachytherapy devices, or components thereof. More particularly, the substrate of the present invention is the component of a catheter, such as the expandable component of a catheter. In a particular embodiment, the expandable component may be an assembly of metal wires or plates, or may be an elastomeric catheter balloon. In a further embodiment, the component may be a metal substrate having ceramic layer formed thereon. In this embodiment, ceramic layer is coated with radioactive coating layer of the present invention. In a still further embodiment, the expandable component is formed from an alloy. Optionally, a protective coating layer is formed over the radioactive coating layer.

The coated expandable component may be expanded or flexibly positioned to rest near or against the walls of the blood vessel to be treated, to deliver a controlled, substantially uniform dose or radiation to the blood vessel wall. In particular, the coated expandable component delivers a dose of beta or gamma radiation. A sheath optionally covers the entire length of the catheter, in order to protect the patient from exposure to radiation during deployment of the catheter. The sheath may be formed, for example, of metal or plastic, and can be retracted or removed from the area of the expandable component of the catheter when the treatment site is reached.

The present invention also relates to a method of making a substrate capable of producing an asymetric radiation field. The asymetric radiation field is created by variations in the amount of radiation in at least one dimension of the substrate. The method of the present invention involves coating the substrate with one or more radioactive coating layers. Optionally, the substrate may be cleaned and surface oxides removed, and may further be coated with a catalytic coating (e.g., a non-radioactive Ni coating). Methods suitable for coating the substrate include electrodeposition, electroless deposition and sol-gel processing. Coating solutions suitable for use in the method include those coatings solutions described herein, including both coating solutions comprising soluble radioisotopes and coating solutions comprising insoluble radioisotopes, as would be ascertainable by one skilled in the art. Substrates suitable for coating according to the present invention include, but are not limited to, metals, alloys, polymers, plastics, ceramics and composites. In a particular embodiment of the present invention, the substrate is a medical device, or a component thereof, formed from materials including, but not limited to, metals, alloys, polymers, plastics, ceramics and composites. In a particular embodiment, the substrate is a brachytherapy device (i.e., a hollow or solid brachytherapy needle). In a further embodiment, the substrate is a stent.

The amount of radiation present on the substrate may vary in several ways. According to a particular embodiment, a brachytherapy needle can be coated with differing concentrations of a radioisotope along the long and/or short axes of the needle. For example, a needle can be coated with varying amounts of a single isotope (e.g., $^{198}$Au) along its longitudinal axis, thereby forming a device capable of producing a radiation field that would be asymetric along the long axis of the needle. According to a further embodiment, a brachytherapy needle can be coated with two or more radioisotopes with similar or differing concentration of either or both radioisotopes along the long and/or short axes of the device. For example, a needle can be coated with a homogenous concentration of a particular radioisotope (e.g., $^{192}$Ir) along its long axis, and further coated with one or more additional radioisotopes (e.g., $^{32}$P, $^{103}$Pd, $^{198}$Au) on at least a portion of the needle, thereby forming a device capable of producing an asymetric radiation field. As a further example, a needle can be coated with an asymetric concentration of an isotope (e.g., $^{192}$Ir) along its long axis, and further coated with one or more additional radioisotopes (e.g., $^{32}$P, $^{103}$Pd, $^{198}$Au) on at least a portion of the needle, thereby forming a device capable of producing an asymetric radiation field.

Coating can be achieved via the methods set forth above, including without limitation, electrodeposition, electroless deposition, and sol-gel processes. More particularly variable coating can be achieved, for example, by multiple coatings and/or through the use of variable masking to cause coatings to selectively deposit in certain areas. One method of masking, for example, involves applying a polymeric coating to areas not intended to receive the radioactive coating. Another method of masking involves selectively activating those areas intended to receive the radioactive coating. The present invention may also employ a sol-gel processes, wherein masking can be achieved, for example, by dipping the substrate into the sol and seeking selective dissolution via partial rehydration of the gel. Alternatively, a variable radioactive coating can be produced by abrasive removal of certain parts of the gel.

The present invention also relates to coated substrates comprising a substrate material and variable radioactive coating or coatings, including but not limited to, medical devices such as brachtherapy devices and stents, which variable coatings produce an inhomogenous radiation field. In a particular embodiment, the coated substrate may further comprise a catalytic coating interposed between the substrate and the variable radioactive coating. Catalytic coatings may also be present between one or more multiple coatings present on the coated substrate in addition to a first radioactive coating. Stents comprising variable radioactive coatings can be implanted, for example, into a blood vessel or any other tubular structure. Brachytherapy devices comprising variable radioactive coatings can be implanted, for example, into tumors.

The present invention also relates to a method of producing a radiation field corresponding to a target field. In a particular embodiment, the present invention relates to a method of producing a radiation field corresponding to the morphology of a tumor. According to this embodiment of the method, one or more radioactively coated brachytherapy devices are designed or chosen based on their characteristic radiation fields to produce a radiation field correspond to the morphology of a particular tumor. The radioactively coated brachytherapy device may be the device described herein, as would be apparent to one skilled in the art. Information on the dosimetry of the radiation fields associated with these devices can be obtained either by calculations or empirically with the measurement of the radiation field produced after the device is placed in a substance that can measure the amount of radiation at known distances from the device. The information can be used to combine different isotopes and devices, and to determine the appropriate placement of devices, and to determine the appropriate placement of the devices so that a radiation field that closely matches the morphology of a tumor can be constructed.

EXAMPLE 1

100 mls of an electroless nickel coating solution was made using two commercially available electroless nickel-phosphorous concentrates, including 6.5 mls of Niklad 1000A and 15 mls of Niklad 1000B, (both from MacDermit, Inc.), the remainder de-ionized water according to Niklad product specifications. This solution was then reduced in volume by evaporating water via heating to approximately 90° C., until the total volume was 80 mls. Subsequently, 7.8 mls of the concentrated solution were placed into a 15 ml test-tube behind a shielded hood, and 2.08 mls of radioactive hypophosphite solution ions (custom synthesized by NEN Life Science Products, containing a mixture of $PO_2$ and $PO_3/PO_4$ in a ratio of approximately 10:90 was added thereto. The total activity added to the test tube was approximately 25 mCi of $^{32}P$, and thus contained approximately 2.5 mCi of $^{32}P$ in the form of hypophosphite ion ($H_2PO_2^-$). The solution was heated to approximately 88° C. on a hot place, with the solution agitated by means of a stir bar.

A catheter sample, the FullFlow™ Device, manufactured by InterVentional Technologies, Inc., was inserted into the solution after having been plated with Ni to activate the surface to be coated, and coated for 40 minutes. Hydrogen bubbles that were produced on the sample surface almost immediately on insertion indicated that the sample was being coated. Bubbling appeared uniform over across the entire sample surface, and the bubbling rate appeared constant over the 40 minute coating period. The device was then removed from the coating solution and rinsed thoroughly.

The radioactivity of the sample was determined using a GM detector. The reading from the GM detector, held next to the catheter after it was rinsed, exceeded 300,000 counts using a 4% efficient GM detector. The catheter was also placed into a liquid scintillation vial and assayed, yielding a reading of 1.08 microcuries.

Figure 2:
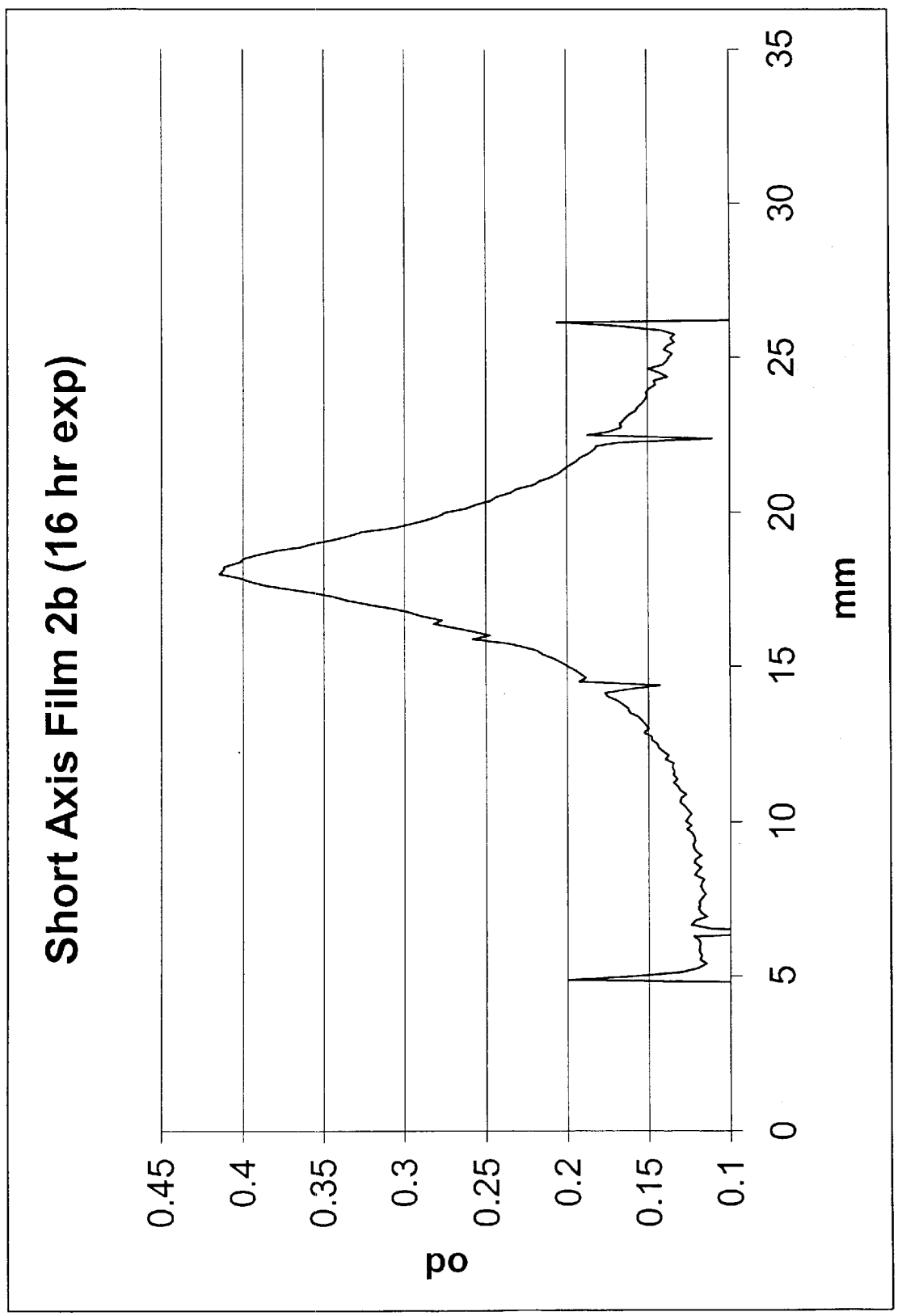
FIG. 2: depicts an isodensity curve of the radioactive coating applied to a catheter according to Example 1, as measured along the catheter's short axis, illustrating uniformity of deposition.
Figure 3:
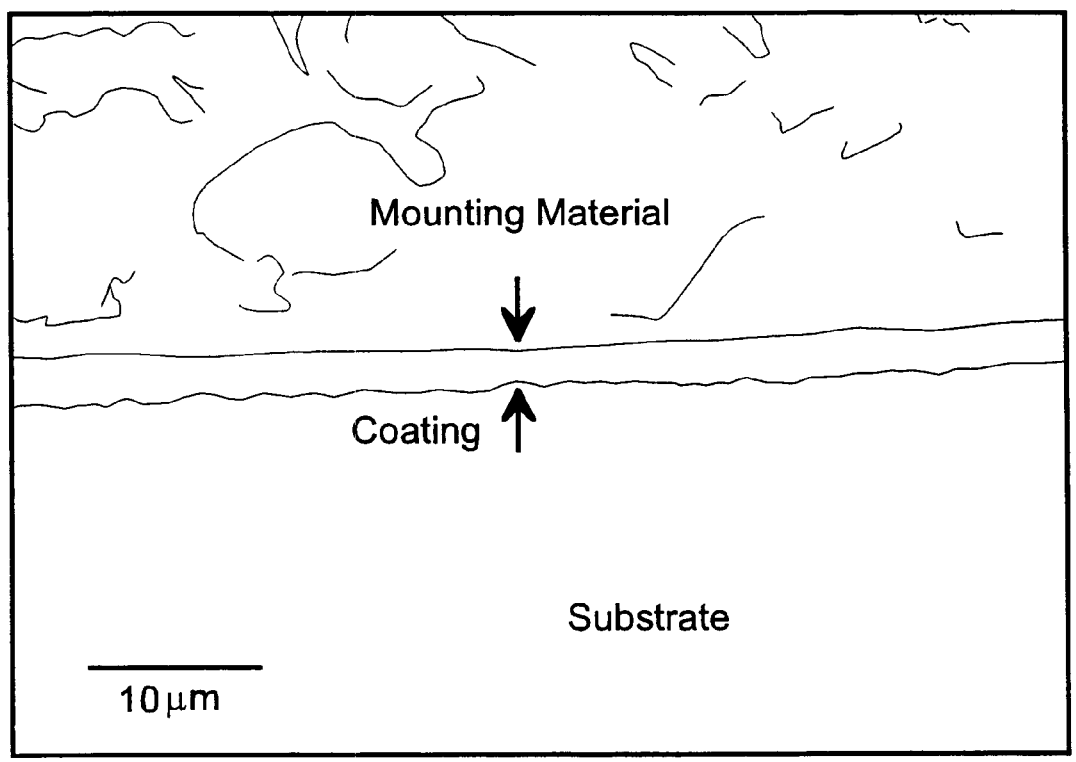
FIG. 3: depicts a Ni-25 at % P electroless coating deposited onto Elgiloy™ in sheet form, viewed in cross-section via scanning electron microscopy (SEM).
Figure 4A:
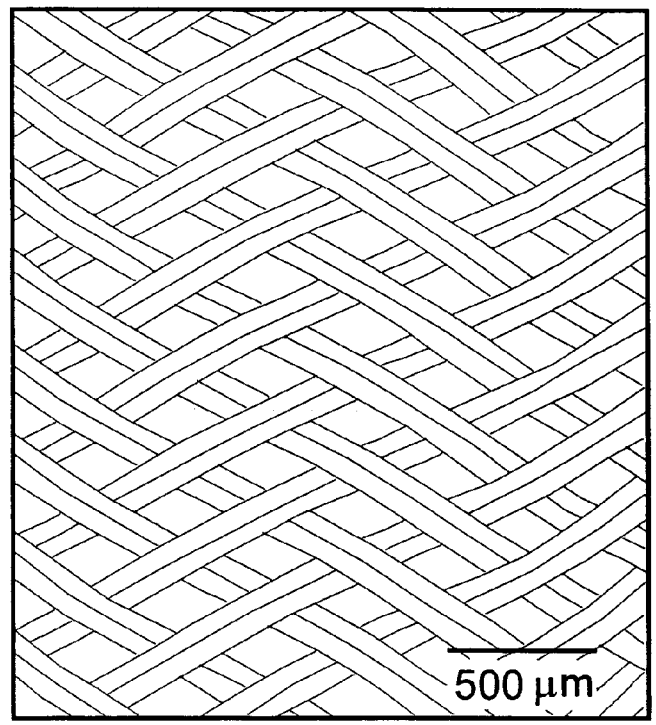
FIG. 4: depicts a coated and uncoated Full Flow catheter component by SEM images. 4A depicts a Full-Flow device coated with a Ni-26 at % P electroless coating. The coating is approximately 7 microns thick, and is uniform in appearance. 4B depicts an uncoated Full-Flow device.
Figure 4B:
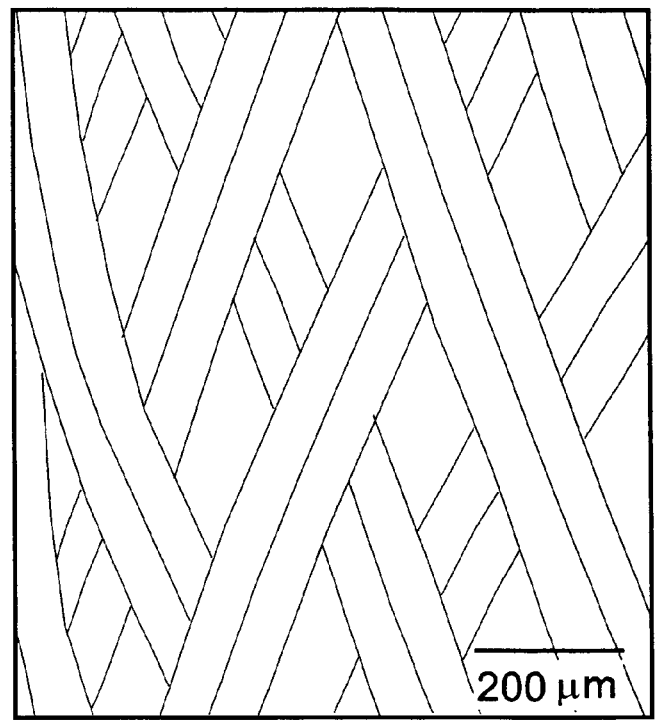
Figure 5A:
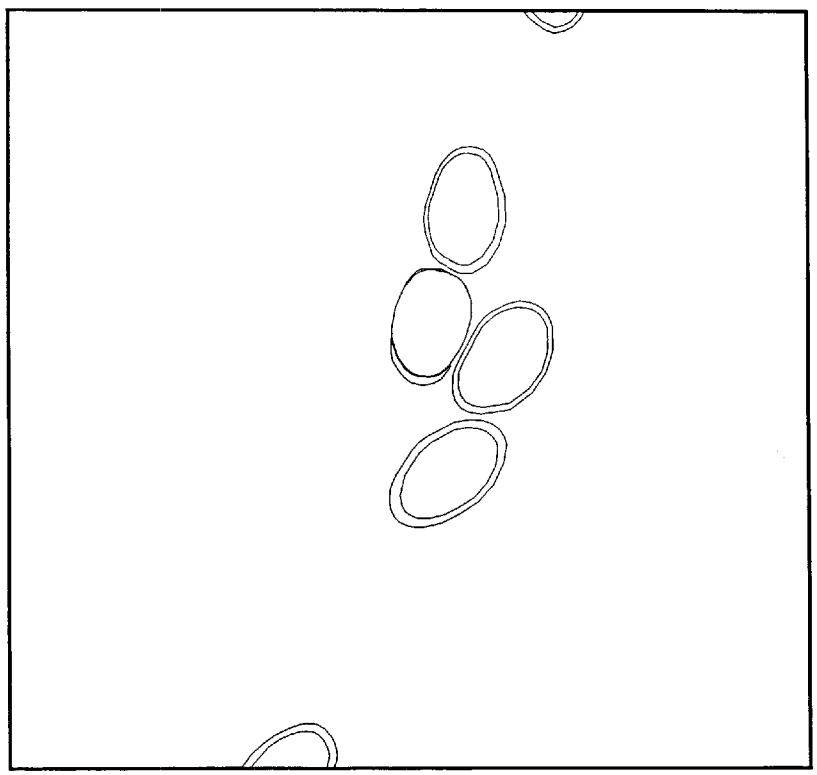
FIG. 5: depicts a cross-section of the Full-Flow device of FIG. 4A. 5A depicts SEM at 100X. 5B depicts SEM at 300X.
Figure 5B:
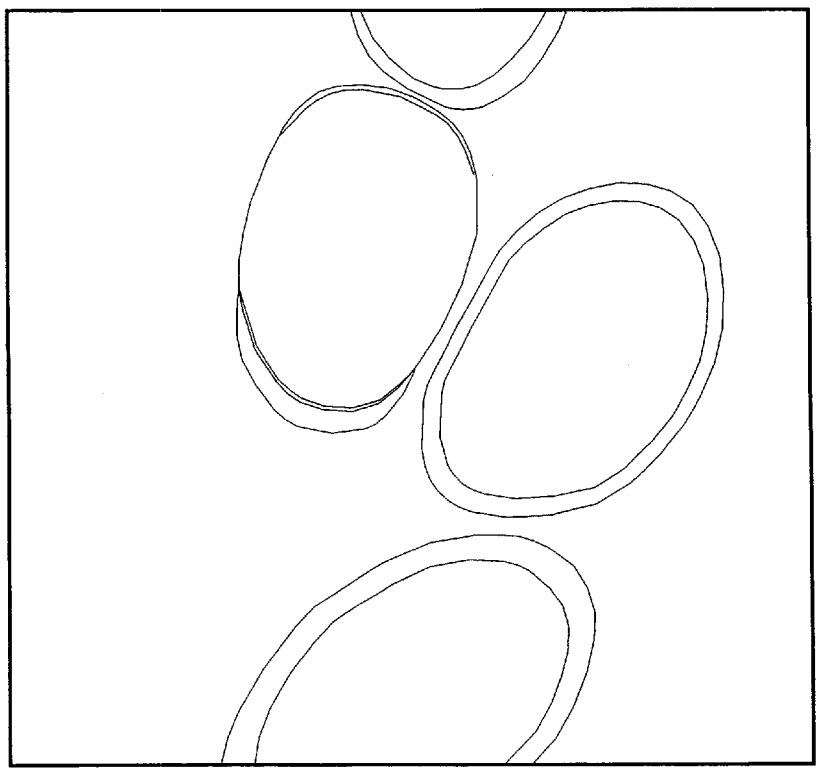
Figure 6:
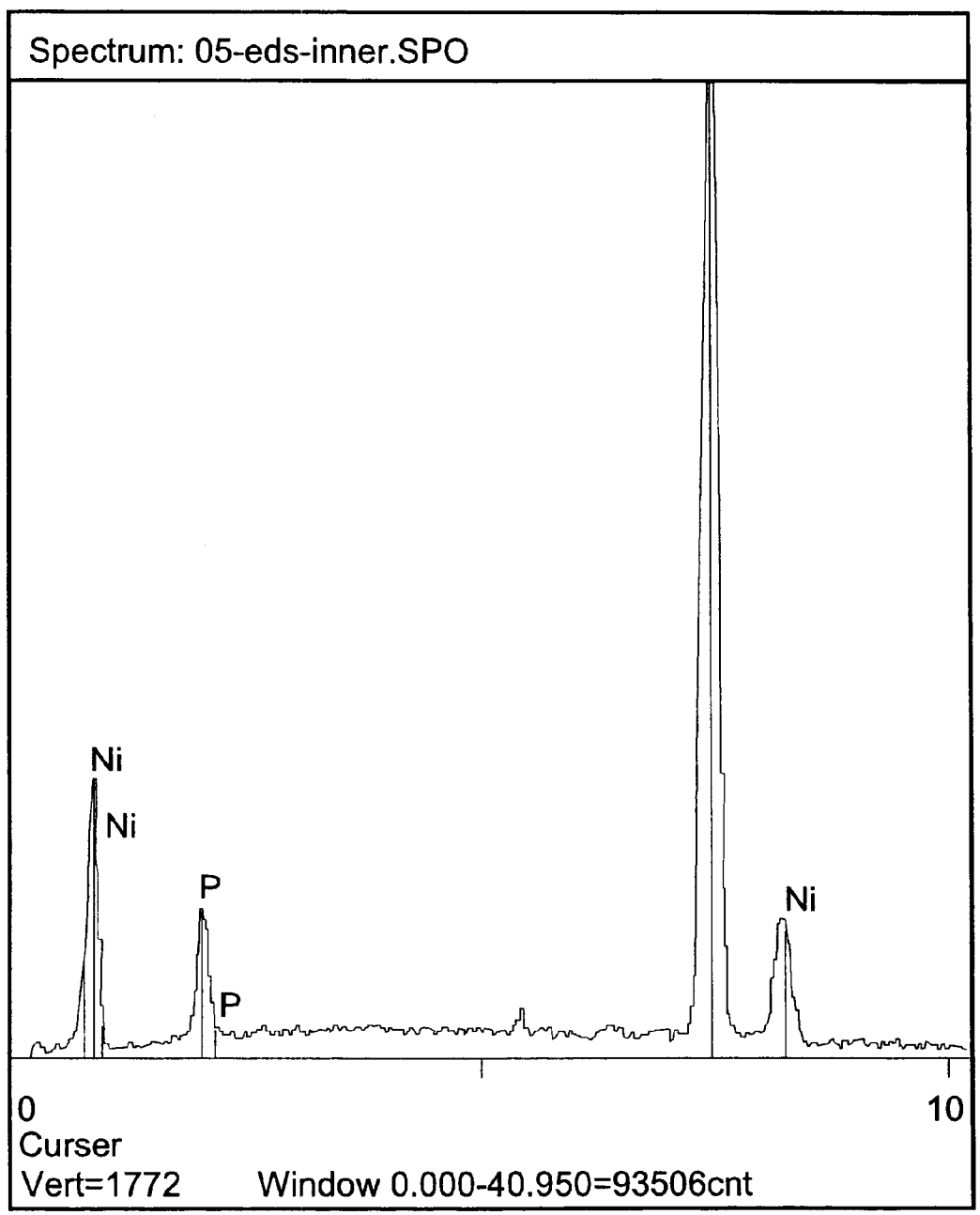
FIG. 6: depicts an energy dispersive x-ray spectrum from a Ni—P electroless electroless coating, showing Ni and P peaks, corresponding quantitative analysis indicates concentration of coating being about 26 mol or atomic % P (or about 15.8 wt. % P).
Figure 7A:
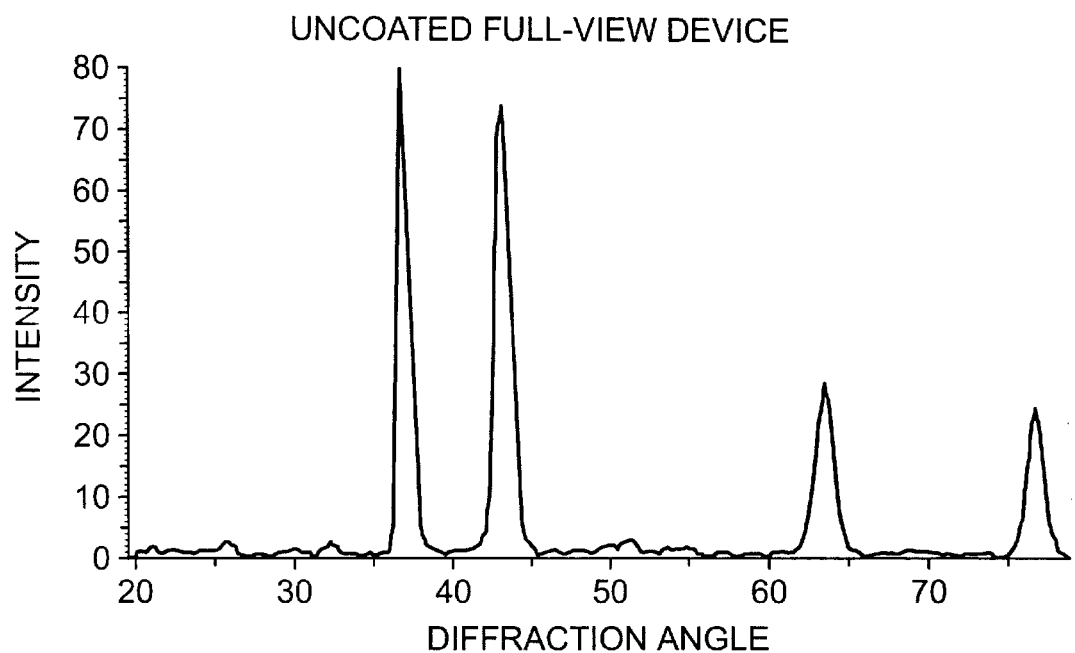
FIG. 7: depicts an x-ray diffraction spectrum the uncoated Eligloy™ and the Ni—P electrolessly coated Elgiloy™ of FIG. 4. The uncoated alloy shows crystalline peaks consistent with the substrate; the coated alloy shows a diffuse peak consistent with the coating being amorphous as expected for a high phosphorus coating.
Figure 7B:
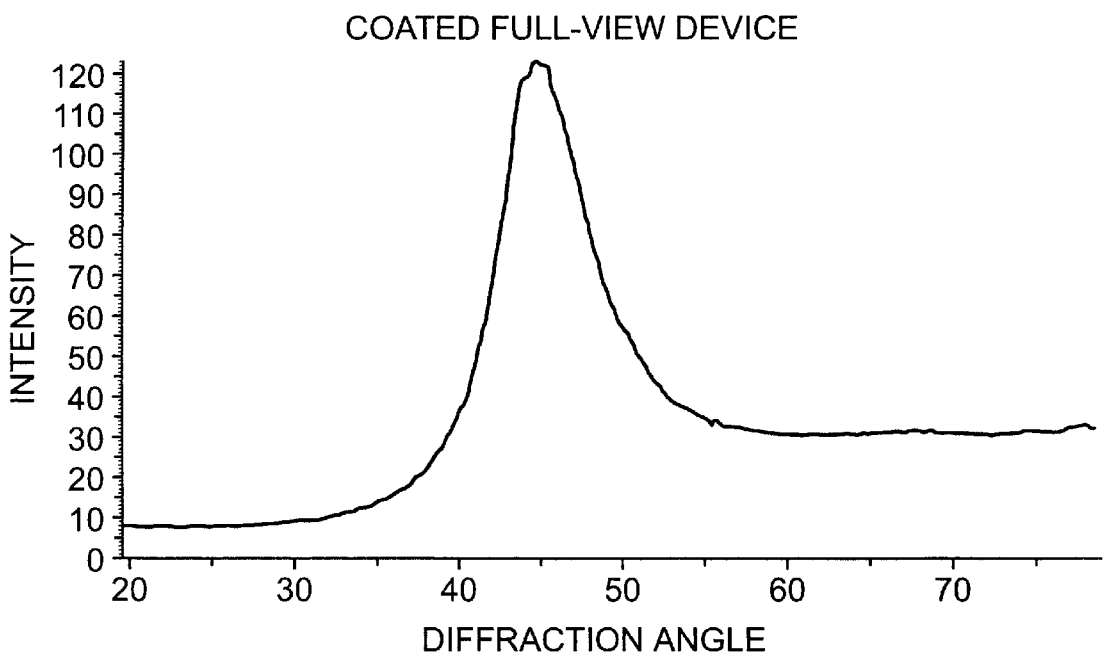

The uniformity of the radioactive coating was characterized by wrapping GAF-chromic film around the catheter for 16 hours. FIG. 1 shows the optical density readings from the film when measured along the catheter's long axis. FIG. 2 shows the optical density readings from the film when measured along the catheter's short axis. Absolute activity is not known, given the absence of a standard. An estimate of the catheter's activity, based upon a 1% yield of hypophosphite in solution to phosphorus on the part, is about 25 $\mu$Ci. This experiment shows that hypophosphite having at least a portion of P as $^{32}P$ when present in an electroless Ni coating solution can indeed cause $^{32}P$-containing Ni—P deposits to be produced. Scale-up of the quantity of $^{32}P$ added to the solution described above by a factor of approximately 1000 would cause a substrate or component to be produced having about 25 mCi of activity, which level of activity is desirable for use in applications involving coronary angioplasty for example.

While the foregoing specification teaches the principles of the present invention, with examples provided for the purpose of illustration, it will be understood that the practice of the invention encompasses all of the usual variations, adaptations, and modifications, as come within the scope of the following claims and their equivalents.

What is claimed is:

1. A radioactive coating solution comprising (1) at least one dissolved carrier metal ion; and (2) either an insoluble radioisotope or an insoluble compound of a radioisotope suspended therein.

2. The radioactive coating solution of claim 1, wherein the carrier metal ion is selected from the group consisting of nickel, copper, chromium, cobalt, palladium, platinum, gold and silver ions.

3. The radioactive coating solution of claim 1, wherein the carrier metal ion present is greater than about 1 g/l and less than about 30 g/l.

4. The radioactive coating solution of claim 3, wherein the carrier metal ion present is from about 3 g/l to about 15 g/l.

5. The radioactive coating solution of claim 1, wherein the insoluble radioisotope is selected from the group consisting of $^{32}P$, $^{90}Y$, and $^{198}Au$.

6. The radioactive coating solution of claim 1, wherein the insoluble compound of radioisotope is selected from the group consisting of FeP, NiP, CoP, SnP, $Ti_4P_3$, and $Y_2O_3$, wherein $^{32}P$, $^{121}Sn$ and $^{90}Y$ are present in significant amounts.

7. The radioactive coating solution of claim 1, wherein a soluble compound of radioisotope is rendered insoluble by encapsulation or immobilization in an insoluble coating or matrix to form the insoluble compound of a radioisotope.

8. The radioactive coating solution of claim 1, wherein the insoluble radioisotope or insoluble compound of a radioisotope present in the coating solution has a specific activity of about 0.1 to about 5000 Ci/g.

9. The radioactive coating solution of claim 1, wherein the insoluble radioisotope is present in the form of particles, said particles from about 5 nm to about 30 $\mu$m in diameter.

10. The radioactive coating solution of claim 1, wherein the solution comprises a copper ion and insoluble $^{32}P$.

11. The radioactive coating solution of claim 1, wherein the solution comprises $CuSO_4$, $H_2SO_4$, and P in particulate form, wherein at least a fraction of the P is $^{32}P$.

12. The radioactive coating solution of claim 1, further comprising a reducing agent.

13. The radioactive coating solution of claim 12, wherein the reducing agent is selecting from the group consisting of hypophosphite, formaldehyde, borohydride, dialkylamine borane and hydrazine.

14. The radioactive coating solution of claim 12, wherein the solution comprises a nickel ion and insoluble $^{198}Au$.

15. The radioactive coating solution of claim 14, wherein the solution comprises $NiSO_4$, $NaH_2PO_4$, Na-acetate, lactice acid, malic acid and Au in particulate form, wherein at least a fraction of the Au is $^{198}Au$.

16. The radioactive coating solution of claim 12, wherein the solution comprises a nickel ion and insoluble $^{90}Y$.

17. The radioactive coating solution of claim 16, wherein the solution comprises $NiSO_4$, $NaH_2PO_4$, Na-acetate, lactice acid, malic acid and $Y_2O_3$ in particulate form, wherein at least a fraction of the Y is $^{90}Y$.

18. The radioactive coating solution of claim 12, wherein the solution comprises a nickel ion and insoluble $^{32}P$.

19. The radioactive coating solution of claim 18, wherein the solution comprises $NiSO_4$, $NaH_2PO_4$, Na-acetate, lactice acid, malic acid and polymer phosphate particles, wherein at least a fraction of the phosphate is $^{32}P$.

20. The radioactive coating solution of claim 19, wherein the polymer phosphate particles are formed by powder processing 2-hydroxyethyl metahacrylate/tert-Bu methacrylate/ehtyl methacrylate phosphorylated with phosphorus oxychloride or polyphosphoric acid.

21. The radioactive coating of claim 1, wherein the insoluble radioisotope is the radioisotope of the carrier metal ion.

22. The radioactive coating of claim 12, wherein the insoluble radioisotope is the radioisotope of an element present in the reducing agent.

23. A method of coating a substrate with a radioactive material by electroless deposition comprising:
    (A) contacting the substrate to be coated with a radioactive coating solution, said solution comprising:
       (1) at least one dissolved carrier metal ion; and
       (2) a reducing agent; and (3) either an insoluble radioisotope or an insoluble compound of a radioisotope suspended therein; under conditions sufficient to chemically deposit a radioactive composite coating onto the substrate; and (B) removing any excess or spent coating solution from the substrate, thereby forming a substrate comprising a radioactive composite coating.

24. The method of claim 23, wherein the carrier metal ion is selected from the group consisting of nickel, copper, chromium, cobalt, palladium, platinum, gold and silver ions.

25. The method of claim 23, wherein the insoluble radioisotope is selected from the group consisting of $^{32}P$, $^{90}Y$, and $^{198}Au$.

26. The method of claim 23, wherein the insoluble compound of radioisotope is selected from the group consisting of FeP, NiP, CoP, SnP, $Ti_4P_3$, and $Y_2O_3$, wherein $^{32}P$, $^{121}Sn$ and $^{90}Y$ are present in significant amounts.

27. The method of claim 23, wherein the insoluble compound of a radioisotope comprises a soluble compound of a radioisotope rendered insoluble.

28. The method of claim 27, wherein the soluble compound of the radioisotope is rendered insoluble by encapsulation or by immobilization in an insoluble coating or matrix.

29. The method of claim 23, wherein the reducing agent is selected from the group consisting of hypophosphite, formaldehyde, borohydride, diaklamine borane and hydrazine.

30. The method of claim 23, wherein the radioactive coating solution comprises a nickel ion and insoluble $^{198}Au$.

31. The method of claim 23, wherein the radioactive coating solution comprises a nickel ion and insoluble $^{90}Y$.

32. The method of claim 23, wherein the radioactive coating solution comprises a nickel ion and insoluble $^{32}P$.

33. The method of claim 32, wherein the solution comprises polymer phosphate particles, wherein at least a fraction of the polymer phosphate particles are $^{32}P$.

34. The method of claim 23, wherein the insoluble radioisotope is the radioisotope of the carrier metal ion.

35. The method of claim 23, wherein the insoluble radioisotope is the radioisotope of an element present in the reducing agent.

36. The method of claim 23, wherein the substrate is a metal.

37. The method of claim 23, wherein the substrate is a polymer.

38. The method of claim 23, wherein the substrate is a ceramic.

39. The method of claim 23, wherein the substrate is a composite material.

40. The method of claim 23, wherein the substrate is an alloy.

41. The method of claim 23, wherein the substrate is a medical device, or a component thereof, selected from the group consisting of catheters, guidewires, brachytherapy devices and stents.

42. The method of claim 41, wherein the substrate is a component of a catheter.

43. The method of claim 42, wherein the component is an expandable component of a catheter.

44. The method of claim 43, wherein the expandable component is formed from a material selected from the group consisting of metal, polymers, alloy, plastics, ceramics and composite materials.

45. The method of claim 44, wherein the expandable component is a metal having a ceramic layer formed thereon.

46. The method of claim 43, wherein the expandable component of a catheter is an elastomeric catheter balloon.

47. The method of claim 46, wherein the substrate to be coated comprises a catalytic coating on the surface thereof.

48. The method of claim 23, further comprising disposing a protective coating over the radioactive coating.

49. The method of claim 23, further comprising:
(C) applying one or more additional radioactive coating layers to said substrate comprising a radioactive composite coating.

50. The method of claim 49, further comprising applying one or more catalytic coating layers between said additional radioactive coating layers.

51. The method of claim 50, wherein the catalytic coating layer is a non-radioactive Ni coating.

52. The method of claim 50, wherein said applying comprises one or more electroless depositions.

53. The method of claim 50, wherein said applying comprises one or more electrodepositions.

54. The method of claim 50, wherein the radioactive composite coating is different from one or more of the additional radioactive coating layers.

55. The method of claim 54, wherein the radioisotope present in the radioactive composite coating is different that a radioisotope present in at least one additional radioactive coating layer.

56. The method of claim 55, wherein the insoluble radioisotope in (A)(3) is $^{198}Au$ and the radioisotope of one or more of the additional radioactive coating layers is $^{32}P$.

57. The method of claim 23, further comprising disposing a protective coating over the outermost radioactive coating.

58. A method of coating a substrate with a radioactive material by electrodeposition comprising:
(A) contacting the substrate with a radioactive coating solution, said solution comprising:
(1) at least one dissolved carrier metal ion; and
(2) either an insoluble radioisotope or an insoluble compound of a radioisotope, under conditions sufficient to electrically deposit a radioactive composite coating onto the substrate;
(B) removing any excess or spent coating solution from the substrate, thereby forming a substrate comprising a radioactive composite coating.

59. The method of claim 58, wherein the carrier metal ion is selected from the group consisting of nickel, copper, chromium, cobalt, palladium, platinum, gold and silver ion.

60. The method of claim 58, wherein the insoluble radioisotope is selected from the group consisting of $^{32}P$, $^{90}Y$, and $^{198}Au$.

61. The method of claim 58, wherein the insoluble compound of radioisotope is selected from the group consisting of FeP, NiP, CoP, SnP, $Ti_4P_3$, and $Y_2O_3$, wherein $^{32}P$, $^{121}Sn$ and $^{90}Y$ are present in significant amounts.

62. The method of claim 58, wherein the insoluble compound of a radioisotope comprises a soluble compound of a radioisotope rendered insoluble.

63. The method of claim 62, wherein the soluble compound of the radioisotope is rendered insoluble by encapsulation or by immobilization in an insoluble coating or matrix.

64. The method of claim 58, wherein the solution comprises a copper ion and the insoluble radioisotope comprises $^{32}P$.

65. The method of claim 64, wherein the solution comprises $CuSO_4$, $H_2SO_4$ and P in particulate form, wherein at least a fraction of P is $^{32}P$.

66. The method of claim 58, wherein the substrate is a metal.

67. The method of claim 58, wherein the substrate is a polymer.

68. The method of claim 58, wherein the substrate is a ceramic.

69. The method of claim 58, wherein the substrate is a composite material.

70. The method of claim 58, wherein the substrate is an alloy.

71. The method of claim 58, wherein the substrate is a medical device, or a component thereof, selecting from the group consisting of catheters, guidewires, stents and brachytherapy devices.

72. The method of claim 58, wherein the substrate is a component of a catheter.

73. The method of claim 72, wherein the component is an expandable component.

74. The method of claim 73, wherein the expandable component is formed from a material selected from the group consisting of metal, polymers, alloy, plastics, ceramics and composite materials.

75. The method of claim 74, wherein the expandable component is a metal having a ceramic layer formed thereon.

76. The method of claim 73, wherein the expandable component of a catheter is an elastomeric catheter balloon.

77. The method of claim 58, further comprising:
(C) applying one or more additional radioactive coating layers to said substrate comprising a radioactive composite coating.

78. The method of claim 77, further comprising (D) applying one or more catalytic coating layers between one or more additional radioactive coating layers.

79. The method of claim 77, wherein said applying comprises one or more electroless depositions.

80. The method of claim 77, wherein said applying comprises one or more electrodepositions.

81. The method of claim 77, wherein the radioactive composite coating is different from one or more of the additional radioactive coating layers.

82. The method of claim 81, wherein the radioisotope of (A)(2) is different than a radioisotope present in one or more of the additional radioactive coating layers.

83. The method of claim 82, wherein the radioisotope of (A)(2) is $^{198}$Au and the radioisotope of the at least one or more radioactive additional layers is $^{32}$P.

84. A radioactive coating solution comprising (1) at least one dissolved carrier metal ion and (2) a dissolved non-metal radioisotope.

85. The radioactive coating solution of claim 84, wherein the dissolved carrier metal ion is selected from the group consisting of nickel, copper, chromium, cobalt, palladium, platinum, gold and silver.

86. The radioactive coating solution of claim 84, wherein the dissolved non-metal radioisotope is $^{32}$P.

87. The radioactive coating solution of claim 86, wherein $^{32}$P is present as an aqueous solution of phosphorous-containing anions.

88. The radioactive coating solution of claim 87, wherein the phosphorous-containing anions comprise one or more of hypophosphite anions, phosphite anions, and phosphate anions.

89. The radioactive coating solution of claim 84, further comprising a reducing agent.

90. The radioactive coating solution of claim 89, wherein the reducing agent is selecting from the group consisting of hypophosphite, formaldehyde, borohydride, dialkylamine borane and hydrazine.

91. The radioactive coating solution of claim 90, wherein the solution comprises $NiSO_4$, $NaH_2PO_2$, Na-acetate, lactic acid and malic acid, wherein at least a fraction of the P is $^{32}$P.

92. The radioactive coating solution of claim 90, wherein the solution comprises AuCN, $NaH_2PO_2$, KCN, wherein at least a fraction of the P is $^{32}$P.

93. The radioactive coating solution of claim 90, wherein the solution comprises $NiSO_4$, NiCl, $NaH_2PO_2$ and $H_3PO_4$, wherein at least a fraction of the P is $^{32}$P.

94. The radioactive coating solution of claim 90, wherein the solution comprises $CrK(SO_4)_2.12H_2O$, $NiSO4-6H_2O$, $(NH_4)_2SO_4$, $NaH_2PO_2$—$H_2O$, $Na_3C_6H_5O_7-2H_2O$, $C_6H_8O_7$, $H_3BO_3$, $(NH_2)_2CS$, $C_{10}H_{16}O$ and $C_{12}H_{25}SO_4Na$, wherein at least a fraction of the P in $NaH_2PO_2$—$H_2O$ is $^{32}$P.

95. A radioactive coating solution comprising (1) at least one dissolved carrier metal ion (2) dissolved $^{198}$Au, and (3) a reducing agent.

96. The radioactive coating solution of claim 95, wherein the dissolved carrier metal ion is selected from the group consisting of nickel, copper, chromium, cobalt, palladium, platinum, gold and silver.

97. The radioactive coating solution of claim 95, wherein the reducing agent is selecting from the group consisting of hypophosphite, formaldehyde, borohydride, dialkylamine borane and hydrazine.

98. The radioactive coating solution of claim 95, wherein the solution comprises AuCN, $NaH_2PO_2$ and KCN, wherein at least a fraction of the Au is $^{198}$Au.

99. The radioactive coating solution of claim 95, wherein the solution comprises AuKCN, KCN, KOH and $KBH_4$, wherein at least a fraction of the Au is $^{198}$Au.

100. A method of coating a substrate with a radioactive material comprising:
(A) contacting the substrate with a solution comprising:
  (1) at least one dissolved carrier metal ion; and
  (2) a reducing agent
  (3) a dissolved radioisotope, under conditions sufficient to chemically deposit a radioactive coating onto the substrate; and
(B) removing any excess or spent coating solution from the substrate, thereby forming a substrate comprising a radioactive coating.

101. The method of claim 100, wherein the carrier metal is selected from the group consisting of nickel, copper, cobalt, palladium, platinum, chromium, gold and silver.

102. The method of claim 100, wherein the radioactive isotope is a beta emitter.

103. The method of claim 102, wherein the beta emitter is selected from the group consisting of $^{14}$C, $^{35}$S, $^{45}$Ca, $^{90}$Sr $^{89}$Sr $^{32}$P, $^{33}$P, $^{3}$H, $^{77}$As, $^{111}$Ag, $^{67}$Cu, $^{166}$Ho, $^{199}$Au, $^{198}$Au, $^{90}$Y, $^{121}$Sn, $^{148}$Pm, $^{149}$Pm, $^{176}$Lu, $^{177}$Lu, $^{106}$Ru, $^{47}$Sc, $^{105}$Rh, $^{131}$I, $^{149}$Sm, $^{153}$Sm, $^{156}$Sm, $^{186}$Re, $^{188}$Re, $^{109}$Pd, $^{165}$Dy, $^{142}$Pr, $^{143}$Pr, $^{144}$Pr, $^{159}$Gd, $^{153}$Gd, $^{175}$Yb, $^{169}$Er, $^{51}$Cr, $^{141}$Ce, $^{147}$Nd, $^{152}$Eu, $^{157}$Tb, $^{170}$Tm, and $^{194}$Ir.

104. The method of claim 100, wherein the radioactive isotope is a gamma emitter.

105. The method of claim 104 wherein the gamma emitter is selected from the group consisting of $^{137}$Cs, $^{60}$Co and $^{192}$Ir.

106. The method of claim 100, wherein the radioactive isotope is a alpha emitter.

107. The method of claim 106, wherein the alpha emitter is selected from the group consisting of $^{226}$Ra and $^{222}$Rn.

108. The method of claim 100, wherein the radioactive isotope is selected from the group consisting of $^{125}$I, $^{192}$Ir and $^{103}$Pd.

109. The method of claim 100, wherein the radioisotope is the radioisotope of the carrier metal.

110. The method of claim 100, wherein the radioisotope is the radioisotope of an element present in the reducing agent.

111. The method of claim 100, wherein the solution comprises an aqueous solution of $NiSO_4$, $NaH_2PO_2.H_2O$, Na-acetate, lactic acid, and malic acid, wherein at least a fraction of the P is $^{32}P$.

112. The method of claim 100, wherein the solution comprises an aqueous solution of AuCN, $NaH_2PO_2.H_2O$, and KCN, wherein at least a fraction of the P is $^{32}P$.

113. The method of claim 100, wherein the solution comprises an aqueous solution of AuCN, $NaH_2PO_2.H_2O$, and KCN, wherein at least a fraction of the Au is $^{198}Au$.

114. The radioactive coating solution of claim 100, wherein the solution comprises AuKCN, KCN, KOH and $KBH_4$, wherein at least a fraction of the Au is $^{198}Au$.

115. The method of claim 100, wherein the substrate is a metal.

116. The method of claim 100, wherein the substrate is a polymer.

117. The method of claim 100, wherein the substrate is a ceramic.

118. The method of claim 100, wherein the substrate is a composite material.

119. The method of claim 100, wherein the substrate is an alloy.

120. The method of claim 100, wherein the substrate is a medical device, or a component thereof, selected from the group consisting of catheters, guidewires, brachytherapy devices and stents.

121. The method of claim 120 wherein the substrate is a component of a catheter.

122. The method of claim 121, wherein the component is an expandable component of a catheter.

123. The method of claim 122, wherein the expandable component is formed from a material selected from the group consisting of metal, polymers, alloy, plastics, ceramics and composite materials.

124. The method of claim 123, wherein the expandable component is a metal having a ceramic layer formed thereon.

125. The method of claim 122, wherein the expandable component of a catheter is an elastomeric catheter balloon.

126. The method of claim 100, wherein the substrate to be coated comprising a catalytic coating on the surface thereof.

127. The method of claim 100, further comprising disposing a protective coating over the radioactive coating.

128. The method of claim 100, further comprising:
(C) applying one or more additional radioactive coating layers to said substrate comprising a radioactive coating.

129. The method of claim 128, further comprising applying one or more catalytic coating layers interposed between one or more additional radioactive coating layers.

130. The method of claim 128, wherein said applying comprises one or more electroless depositions.

131. The method of claim 128, wherein said applying comprises one or more electrodepositions.

132. The method of claim 128, wherein the radioactive coating is different from one or more additional radioactive coating layers.

133. The method of claim 132, wherein the radioisotope of at least one of said additional radioactive coating layers is different from said dissolved radioisotope in (A)(3).

134. A method of coating a substrate with a radioactive material, comprising contacting the substrate with a radioactive coating solution, under conditions sufficient to electrically deposit a radioactive coating onto the substrate, said coating solution comprising (1) at least one dissolved carrier metal and (2) a dissolved non-metal radioisotope, thereby forming a substrate comprising a radioactive coating.

135. The method of claim 134, wherein the dissolved-non metal radioisotope is $^{32}P$.

136. The method of claim 135, where the P is $^{32}P$ is present as an aqueous solution of phosphorus-containing anions.

137. The method of claim 136, wherein the phosphorus-containing anions comprise one or more of hypophosphite anions, phosphite anions, and phosphate anions.

138. The method of claim 134, wherein the substrate is a metal.

139. The method of claim 134, wherein the substrate is a polymer.

140. The method of claim 134, wherein the substrate is a ceramic.

141. The method of claim 134, wherein the substrate is a composite material.

142. The method of claim 134, wherein the substrate is an alloy.

143. The method of claim 134, wherein the substrate is an expandable component of a catheter.

144. The method of claim 143, wherein the expandable component is formed from material selected from the group consisting of metal, polymers, alloy, plastics, ceramics and composite materials.

145. The method of claim 144, wherein the expandable component is a metal having a ceramic layer formed thereon.

146. The method of claim 143, wherein the expandable component of a catheter is an elastomeric catheter balloon.

147. The method of claim 134, further comprising disposing a protective coating over the radioactive coating.

148. The method of claim 134, further comprising:
(3) applying one or more additional radioactive coating layers to said substrate comprising a radioactive coating.

149. The method of claim 148, further comprising applying one or more catalytic coating layers interposed between one or more additional radioactive coating layers.

150. The method of claim 148, wherein said applying comprises one or more electroless depositions.

151. The method of claim 148, wherein said applying comprises one or more electrodepositions.

152. The method of claim 148, wherein radioactive coating layer is different than at least one of the one or more additional radioactive coating layers.

153. The method of claim 152, herein the radioisotope of the radioactive coating layer is different than a radioisotope of at least one of the one or more additional radioactive coating layers.

154. A method of coating a substrate with a radioactive material, comprising contacting the substrate with a radioactive coating solution, under conditions sufficient to electrically deposit a radioactive coating onto the substrate, said coating solution comprising (1) at least one dissolved carrier metal and (2) dissolved $^{198}Au$, thereby forming a substrate comprising a radioactive coating.

155. A coated substrate comprising at least a first layer of a radioactive composite coating, which comprises a metal matrix and a radioactive phase dispersed therein, disposed on a substrate material, wherein said radioactive phase comprises an insoluble radioisotope or an insoluble compound of a radioisotope.

156. The coated substrate of claim 155, wherein the metal matrix comprises a metal selected from the group consisting of nickel, copper, chromium, cobalt, platinum, palladium, gold and silver.

157. The coated substrate of claim 155, wherein the insoluble radioisotope is selected from the group consisting of $^{32}P$, $^{90}Y$ and $^{198}Au$.

158. The coated substrate of claim 155, wherein the insoluble compound of a radioisotope is selected from the group consisting of FeP, NiP, CoP, SnP, $Ti_4P_3$ and $Y_2O_3$, wherein $^{32}P$, $^{121}Sn$ and $^{90}Y$ are present in significant amounts.

159. The coated substrate of claim 155, wherein the insoluble compound of a radioisotope comprises a soluble compound of a radioisotope rendered insoluble.

160. The coated substrate of claim 159, wherein the soluble compound of the radioisotope is rendered insoluble by encapsulation or by immobilization in an insoluble coating or matrix.

161. The coated substrate of claim 155, wherein the first layer is from about 0.1 to about 20 $\mu$m thick.

162. The coated substrate of claim 161, wherein the first layer is from about 1.0 to about 2.0 $\mu$m thick.

163. The coated substrate of claim 155, wherein the insoluble radioisotope or insoluble compound of a radioisotope is present in the form of particles, said particles from about 5 mn to about 30 $\mu$m in diameter.

164. The coated substrate of claim 155, further comprising a catalytic coating layer interposed between the substrate and the first layer of the radioactive composite coating.

165. The coated substrate of claim 164, wherein the catalytic coating comprises nickel.

166. The coated substrate of claim 155, wherein one or more additional layers of radioactive coating is disposed on said first layer.

167. The coated substrate of claim 166, wherein the first layer is different than at least one of the one or more additional layers of radioactive coating.

168. The coated substrate of claim 167, wherein the first layer comprises an insoluble radioisotope that is different than a radioisotope present in at least one of the one or more additional layers of radioactive coating.

169. The coated substrate of claim 167, further comprising one or more catalytic coating layers interposed between one or more additional radioactive coating layers.

170. The coated substrate of claim 169, one or more of the catalytic coating layers comprises Ni.

171. The coated substrate of claim 155, wherein the substrate is a metal.

172. The coated substrate of claim 155, wherein the substrate is a polymer.

173. The coated substrate of claim 155, wherein the substrate is a ceramic.

174. The coated substrate of claim 155, wherein the substrate is a composite substrate.

175. The coated substrate of claim 155, wherein the substrate is an alloy.

176. The coated substrate of claim 155, wherein the substrate is a medical device, or a component thereof, selecting from the group comprising catheters, guidewires, stents and brachytherapy devices.

177. The coated substrate of claim 176, wherein the substrate is a component of a catheter.

178. The coated substrate of claim 177, wherein the substrate is an expandable component of a catheter.

179. The coated substrate of claim 178, wherein the expandable component is Formed from material selected from the group consisting of metal, polymers, alloy, plastics, ceramics and composite materials.

180. The coated substrate of claim 179, wherein the expandable component is a metal having a ceramic layer formed thereon.

181. The coated substrate of claim 178, wherein the expandable component of a catheter is an elastomeric catheter balloon.

182. The coated substrate of claim 155, further comprising disposing a protective coating over the radioactive coating.

183. A radioactive delivery catheter comprising a component having at least a first layer of radioactive coating thereon, wherein said radioactive coating is formed from a radioactive coating solution comprising (1) at least one dissolved carrier metal ion; and (2) either an insoluble radioisotope or an insoluble compound of a radioisotope suspended therein.

184. The radioactive delivery catheter of claim 183, wherein the carrier metal is selected from the group consisting of nickel, copper, chromium, gold and silver.

185. The radioactive delivery catheter of claim 183, wherein the radioisotope is a beta emitter.

186. The radioactive delivery catheter of claim 185, wherein the beta emitter is selected from the group consisting of $^{14}C$, $^{35}S$, $^{45}Ca$, $^{90}Sr$, $^{89}Sr$, $^{32}P$, $^{33}P$, $^{3}H$, $^{77}As$, $^{111}Ag$, $^{67}Cu$, $^{166}Ho$, $^{199}Au$, $^{198}AU$, $^{90}Y$, $^{121}Sn$, $^{148}Pm$, $^{149}Pm$, $^{176}Lu$, $^{177}Lu$, $^{106}Ru$, $^{47}Sc$, $^{105}Rh$, $^{131}I$, $^{149}Sm$, $^{153}Sm$, $^{156}Sm$, $^{186}Re$, $^{188}Re$, $^{109}Pd$, $^{165}Dy$, $^{142}Pr$, $^{143}Pr$, $^{144}Pr$, $^{159}Gd$, $^{153}Gd$, $^{175}Yb$, $^{169}Er$, $^{51}Cr$, $^{141}Ce$, $^{147}Nd$, $^{152}Eu$, $^{157}Tb$, $^{170}Tm$, and $^{194}Ir$.

187. The radioactive delivery catheter of claim 183, wherein the radioisotope is a gamma emitter.

188. The radioactive delivery catheter of claim 187, wherein the gamma emitter is selected from the group consisting of $^{137}Cs$, $^{60}Co$ and $^{192}Ir$.

189. The radioactive delivery catheter of claim 183, wherein the radioisotope is a alpha emitter.

190. The radioactive delivery catheter of claim 189, wherein the alpha emitter is selected from the group consisting of $^{226}Ra$ and $^{222}Rn$.

191. The radioactive delivery catheter of claim 183, wherein the radioisotope is selected from the group consisting of $^{125}I$, $^{192}Ir$ and $^{103}Pd$.

192. The radioactive delivery catheter of claim 183, further comprising a catalytic coating interposed between the component and the radioactive coating.

193. The radioactive delivery catheter of claim 192, wherein the catalytic coating comprises nickel.

194. The radioactive delivery catheter of claim 183, further comprising one or more additional layers of radioactive coating disposed thereon.

195. The radioactive delivery catheter of claim 194, wherein the first layer of radioactive coating is different than at least one of the one or more additional layers of radioactive coating.

196. The radioactive delivery catheter of claim 195, wherein the first layer comprises a radioisotope that is different from a radioisotope of at least one of the one or more additional layers of radioactive coating.

197. The radioactive delivery catheter of claim 183, further comprising a protective layer disposed over the radioactive coating.

198. A brachytherapy device comprising:
(a) a substrate; and
(b) at least a first radioactive coating layer formed from a radioactive coating solution comprising (1) at least one dissolved carrier metal ion; and (2) either an insoluble radioisotope or an insoluble compound of a radioisotope suspended therein, wherein said radioactive coating layer is formed on said substrate and has a total radioactivity that varies in at least one dimension of the device.

199. The brachytherapy device of claim 198, wherein the substrate is a hollow needle.

200. The brachytherapy device of claim 198, wherein the substrate is a solid needle.

201. The brachytherapy device of claim 198, wherein the first radioactive coating layer comprises a variable concentration of a radioisotope along said dimension.

202. The branchytherapy device of claim 198, further comprising one or more additional radioactive coating layers covering at least a portion thereof.

203. The brachytherapy device of claim 202, wherein the first radioactive coating layer is different from at least one of the one or more additional radioactive coating layers.

204. The brachytherapy device of claim 203, wherein the first radioactive coating layer comprises $^{192}$Ir and said one or more additional radioactive coating layers comprises a radioisotope selected from the group consisting of $^{32}$P, $^{103}$Pd and $^{198}$Au.

205. The brachytherapy device of claim 202, wherein one or both of the first radioactive coating layer and the additional radioactive coating layers comprise a variable concentration of radioisotope along said dimension.

206. The brachytherapy device of claim 198, wherein the radioactive coating comprises a metal matrix and a radioactive dispersed phase.

207. The brachytherapy device of claim 198, further comprising a catalytic coating layer interposed between the substrate and the first radioactive coating layer.

208. The brachytherapy device of claim 198, further comprising one or more catalytic coating layers interposed between one or more additional radioactive coating layers.

* * * * *